United States Patent
Moffitt et al.

(10) Patent No.: US 7,742,810 B2
(45) Date of Patent: Jun. 22, 2010

(54) SHORT DURATION PRE-PULSING TO REDUCE STIMULATION-EVOKED SIDE-EFFECTS

(75) Inventors: Michael A. Moffitt, Valencia, CA (US); David K. L. Peterson, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 415 days.

(21) Appl. No.: 11/752,895

(22) Filed: May 23, 2007

(65) Prior Publication Data

US 2008/0294226 A1 Nov. 27, 2008

(51) Int. Cl.
*A61N 1/05* (2006.01)
(52) U.S. Cl. .............. 607/2; 607/46; 607/66; 607/68; 607/117; 607/118
(58) Field of Classification Search ........... 607/2, 607/46, 66, 68, 117–118
See application file for complete search history.

(56) References Cited

U.S. PATENT DOCUMENTS

| | | | |
|---|---|---|---|
| 5,097,833 A | 3/1992 | Campos | |
| 5,117,826 A | 6/1992 | Bartelt et al. | |
| 6,421,566 B1 | 7/2002 | Holsheimer | |
| 6,516,227 B1 | 2/2003 | Meadows et al. | |
| 6,560,490 B2 | 5/2003 | Grill et al. | |
| 6,609,031 B1* | 8/2003 | Law et al. ............. | 607/46 |
| 6,675,046 B2 | 1/2004 | Holsheimer | |
| 6,850,802 B2 | 2/2005 | Holsheimer | |
| 6,892,097 B2 | 5/2005 | Holsheimer | |
| 6,895,280 B2 | 5/2005 | Meadows et al. | |
| 6,944,501 B1* | 9/2005 | Pless ..................... | 607/45 |
| 6,993,384 B2 | 1/2006 | Bradley et al. | |
| 7,539,538 B2 | 5/2009 | Parramon et al. | |
| 2002/0123780 A1 | 9/2002 | Grill et al. | |
| 2003/0139781 A1 | 7/2003 | Bradley et al. | |
| 2004/0127953 A1* | 7/2004 | Kilgore et al. ......... | 607/46 |
| 2005/0267546 A1 | 12/2005 | Parramon et al. | |
| 2006/0122660 A1 | 6/2006 | Boveja et al. | |
| 2007/0038250 A1 | 2/2007 | He et al. | |
| 2008/0294211 A1 | 11/2008 | Moffitt | |

OTHER PUBLICATIONS

Grill, W., et al., "Inversion of the Current-Distance Relationship by Transient Depolarization", IEEE Transactions of Biomedical Engineering, vol. 44, No. 1, pp. 1-9, Jan. 1997.

(Continued)

*Primary Examiner*—Carl H Layno
*Assistant Examiner*—Erica Lee
(74) *Attorney, Agent, or Firm*—Vista IP Law Group LLP

(57) ABSTRACT

A method and neurostimulation system of providing therapy to a patient is provided. At least one electrode is placed in contact with tissue of a patient. A sub-threshold, hyperpolarizing, conditioning pre-pulse (e.g., an anodic pulse) is conveyed from the electrode(s) to render a first region of the tissue (e.g., dorsal root fibers) less excitable to stimulation, and a depolarizing stimulation pulse (e.g., a cathodic pulse) is conveyed from the electrode(s) to stimulate a second different region of the tissue (e.g., dorsal column fibers). The conditioning pre-pulse has a relatively short duration (e.g., less than 200 μs).

25 Claims, 15 Drawing Sheets

OTHER PUBLICATIONS

McIntyre, C., et al., "Selective Microstimulation of Central Nervous System Neurons", Annals of Biomedical Engineering, vol. 28, pp. 219-233, 2000.

Blumental, T.D., PhD., et al., "Prepulses Reduce the Pain of Cutaneous Electrical Shocks", Psychosomatic Medicine, 63:275-281, 2000.

Poletto, C.J., et al., "Elevating Pain Threshold in Humans Using Depolarizing Prepulses", IEEE Transactions on Biomedical Engineering, vol. 49, No. 10, pp. 1221-1224, Oct. 2002.

Hennings, K., et al., "Selective Activation of Small-Diameter Motor Fibres Using Exponentially Rising Waveforms: a theoretical study", Medical & Biological Engineering & Computing, vol. 43, pp. 493-500, 2005.

Holsheimer, J., et al., "Effects of Electrode Geometry and Combination on Nerve Fibre Selectivity in Spinal Cord Stimulation", Med. & Biol. Eng. & Comput, 33:676-682, 1995.

Gorman, Peter H. and Mortimer, Thomas J., The effect of Stimulus Parameters on the Recruitment Characteristics of Direct Nerve Stimulation, IEEE-TBME, vol. BME-30, No. 7, pp. 407-414, Jul. 1983.

Deep-Brain Stimulation of the Subthalamic Nucleus or the Pars Interna of the Globus Pallidus in Parkinson's Disease, N Engl J. Med., vol. 345, No. 13, pp. 956-963, Sep. 27, 2001.

PCT International Search Report for PCT/US2008/006125, Applicant: Boston Scientific Neuromodulation Corporation, Form PCT/ISA/210 and 220, dated Sep. 25, 2008 (7 pages).

PCT Written Opinion of the International Search Authority for PCT/US2008/006125, Applicant: Boston Scientific Neuromodulation Corporation, Form PCT/ISA/237, dated Sep. 25, 2008 (7 pages).

* cited by examiner

SHORT DURATION PRE-PULSING TO REDUCE STIMULATION-EVOKED SIDE-EFFECTS

FIELD OF THE INVENTION

The present invention relates to tissue stimulation systems, and more particularly, to a system and method for conditioning and stimulating nerve tissue.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the stimulation lead(s) to stimulate or activate a volume of nerve tissue in accordance with a set of stimulation parameters and provide the desired efficacious therapy to the patient. Typically, this nerve tissue constitutes myelinated nerve tissue (i.e., "white matter), which can be understood as the parts of the brain and spinal cord responsible for information transmission (axons). A typical stimulation parameter set may include the electrodes that are sourcing (anodes) or returning (cathodes) the stimulation pulses at any given time, as well as the magnitude, duration, and rate of the stimulation pulses. A neurostimulation system further comprise a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer Station (CPS), which typically includes a general purpose computer, such as a laptop, with a programming software package installed thereon.

The best stimulus parameter set will typically be one that provides stimulation energy to the volume of nerve tissue that must be stimulated in order to provide the therapeutic benefit (e.g., pain relief), while minimizing the volume of non-target nerve tissue that is stimulated. However, because the target nerve tissue (i.e., the tissue associated with the therapeutic effects) and non-target nerve tissue (i.e., the tissue associated with undesirable side effects) are often juxtaposed, therapeutically stimulating nerve tissue while preventing side effects may be difficult to achieve.

For example, in SCS, stimulation of the spinal cord creates the sensation known as paresthesia, which can be characterized as an alternative sensation that replaces the pain signals sensed by the patient. To produce the feeling of paresthesia without inducing involuntary motor movements within the patient, it is often desirable to preferentially stimulate nerve fibers in the dorsal column (DC nerve fibers), which primarily include sensory nerve fibers, over nerve fibers in the dorsal roots (DR nerve fibers), which include both sensory nerve fibers and motor reflex nerve fibers.

However, this can be difficult to accomplish, since the DR nerve fibers have larger diameters than the largest nearby DC nerve fibers, and thus, have a lower threshold at which they are excited. Other factors that contribute to the lower threshold needed to excite DR nerve fibers are the different orientations of the DC nerve fibers and DR nerve fibers, the curved shape of the DR nerve fibers, and the inhomogeneity and anisotropy of the surrounding medium at the entrance of the DR nerve fibers into the spinal cord. Thus, action potentials may still be evoked in DR nerve fibers at lower voltages than with nearby DC nerve fibers. As a result, the DC fibers that are desired to be stimulated have a lower probability to be stimulated than do the DR fibers.

For reasons such as this, it is often desirable to modify the threshold at which nerve tissue is activated in a manner that maximizes excitation of the target nerve tissue, while minimizing excitation of the non-target nerve tissue. Currently, this can be accomplished by applying a depolarizing conditioning pulse (or pre-pulse) to render nerve tissue (and in this case, the non-target nerve tissue) less excitable to the subsequent stimulation pulse and/or applying a hyperpolarizing conditioning pulse to render tissue (and in this case, target nerve tissue) more excitable to the subsequent stimulation pulse. For example, a depolarizing conditioning pulse can be applied to non-target nerve tissue via a first electrode to reduce its excitability just prior to applying a stimulation pulse to the target nerve tissue via a second electrode. Or a hyperpolarizing conditioning pulse can be applied to target nerve tissue via an electrode to increase its excitability just prior to applying a stimulation pulse to the target nerve tissue via the same electrode.

To better understand the effect of conditioning and stimulation pulses on nerve tissue, reference to FIG. 1 will now be made. As there shown, a typical neuron 10 that can be found in the white matter of the spinal cord or brain includes an axon 12 containing ionic fluid (and primarily potassium and sodium ions) 14, a myelin sheath 16, which is formed of a fatty tissue layer, coating the axon 12, and a series of regularly spaced gaps 18 (referred to as "Nodes of Ranvier"), which are typically about 1 micrometer in length and expose a membrane 20 of the axon 12 to extracellular ionic fluid 22. When an action potential (i.e., a sharp electrochemical response) is induced within the neuron 10, the transmembrane voltage potential (i.e., a voltage potential that exists across the membrane 20 of the axon 12) changes, thereby conducting a neural impulse along the axon neuron 10 as sodium and potassium ions flow in and out of the axon 12 via the membrane 20. Because ion flow can only occur at the nodes 18 where the membrane 20 of the axon 12 is exposed to the extracellular ionic fluid 22, the neural impulse will actually jump along the axon 12 from one node 16 to the next node 16. In this manner, the myelin sheath 16 serves to speed the neural impulse by insulating the electrical current and making it possible for the impulse to jump from node 16 to node 16 along the axon 12, which is faster and more energetically favorable than continuous conduction along the axon 12.

As shown in FIGS. 2a-2d, the flow of sodium and potassium ions through a membrane 20 of the axon 12 is controlled by a cluster of voltage-gated ion channels concentrated within each node 16. In general, ion-channels are pore-forming proteins that help to establish and control the small voltage gradient that exists across the plasma membrane of all living cells by allowing the flow of ions down their electrical chemical gradient. Broadly speaking, the ion channels can be categorized as either sodium ion channels 24 (only one shown), which selectively open to allow sodium ions ($Na^-$) from the ionic extracellular ionic fluid 22 to enter through the membrane 20 into the axon 12, or potassium ion channels 26 (only one shown), which selectively open to allow potassium ions ($K^-$) to exit the axon 12 into the extracellcellular ionic fluid 22 via the membrane 20. Each of the sodium ion channels 24 includes an activation gate referred to as an "m-gate" 28, which opens or activates the respective sodium ion channel 24, and an inactivation gate referred to as an "h-gate" 30, which closes or inactivates the respective sodium ion channel 24. Each of potassium ion channels 26 includes an activation gate referred to as an "n-gate" 32, which opens or activates the respective potassium ion channel 26. The threshold at which the axon 12 is activated or not activated is controlled by the coordination of the opening and closing of these ion channels via their respective gates, with the threshold being an "all or nothing" phenomenon; that is, an action potential will either be evoked in the axon or not at all.

Referring further to FIG. 3, the operation and timing of the ion channels 24, 26 will now be described in generating an action potential within the axon 12. Normally, when the axon 12 is at rest, the interior of the axon 12 has a transmembrane voltage potential (i.e., the voltage potential of the interior relative to the exterior of the axon 12) of −70 to −80 mV. Ultimately, the transmembrane voltage potential will depend largely upon the percentage of sodium ion channels 24 and potassium ion channels 26 that are open. Because each of the channels have different voltage potentials, a percentage of the sodium ion channels 24 and potassium ion channels 26 will be open at any given time, with the chance that an action potential being evoked increasing as the percentage of these ion channels being open increases.

When the axon 12 is at rest (point A in FIG. 3), a large percentage of the sodium ion channels 24 and potassium ion channels 26 are closed. At this resting potential (in this case, −70 mV), for each closed sodium ion channel 24, the m-gate 28 will be closed, while the h-gate 30 will be open, and for each closed potassium ion channel 26, the n-gate 32 will be closed, as illustrated in FIG. 2a. In this state, none of the sodium ions can enter the interior of the axon 12 via the closed sodium ion channels 24, and none of the potassium ions can exit the interior of the axon 12 via the closed potassium ion channels 26.

In response to a stimulation pulse (point B in FIG. 3), which can be defined as an electrical signal that is large enough to evoke an action potential within the axon 12, the negative transmembrane voltage potential moves toward a more positive excitation threshold, thereby causing a large percentage of the m-gates 28 to rapidly open, while slowly closing a large percentage of the h-gates 30 and slowly opening a large percentage of the n-gates 32, as illustrated in FIG. 2b. Because activation of the sodium ion channels 24 (opening of the m-gates 28) is faster than inactivation of the sodium ion channels 24 (closing of the h-gates 30), transient opening of the sodium ion channels 24 occurs, thereby allowing sodium ions to rush into the interior of the axon 12. Also, because activation of the sodium ion channels 24 is faster than activation of the potassium ion channels 26 (opening of the n-gates 32), the influx of sodium current (ions) exceeds the efflux of potassium current (ions), resulting in change of the transmembrane voltage to a more positive value and approaching a threshold value (i.e., the transmembrane voltage potential at which an action potential is evoked, and in this case −55 mV) (point C in FIG. 3). The transmembrane voltage potential then decreases rapidly, depolarizing axon 12 (high positive slope curve between point C and point D of FIG. 3).

When the change in transmembrane voltage potential reaches a certain level (in this case 30 mV) (point D in FIG. 3), a large percentage of the n-gates 32 are open to maintain activation of the potassium ion channels 26, while a large percentage of the h-gates 30 are completely closed to inactivate the sodium ion channels 24, as shown in FIG. 2c. As a result, the efflux of potassium current exceeds the influx of sodium current, resulting in a rapid change of the transmembrane voltage (becomes more negative), repolarizing the axon 12 (negative slope curve between point D and point E of FIG. 3). When the increase in transmembrane voltage potential reaches the resting voltage potential (point E of FIG. 3), a large percentage of the n-gates 32 remain open, allowing the efflux of potassium current through the potassium ion channels 26 to continue, thereby causing the negative change in the transmembrane electrical potential to continue beyond the resting electrical potential; that is, the axon 12 becomes hyperpolarized (point F of FIG. 3). At this point, the m-gates 28 rapidly close, while the h-gates 30 slowly open and the n-gates 32 slowly close during a refractory period, so that the axon 12 returns to its resting period (point G in FIG. 3) until another stimulation signal is applied to the axon 12.

Like stimulation pulses, conditioning pre-pulses manipulate the opening and closing of sodium ion channels 24 and potassium ion channels 26 to change the transmembrane voltage potential. Unlike stimulation pulses, conditioning pre-pulses are applied at an amplitude that does not evoke an action potential within the axon 12.

For example, a relatively long (e.g., 500 μs or more, with 1 ms being typical) depolarizing pre-pulse applied to the axon 12 at a relatively low level will initially increase the percentage of the h-gates 30 that are partially or completely closed without evoking an action potential in the axon 12, thereby deactivating more sodium ion channels 24. As a result, the action potential threshold of the axon 12 (i.e., the stimulation amplitude level at which an action potential is evoked in the axon) will be increased, since the stimulation pulse must activate a greater percentage of sodium ion channels 24 to evoke an action potential in the axon. Thus, a stimulation pulse applied soon after a long depolarizing pre-pulse will need to be stronger to evoke the action potential within the axon 12 relative to a stimulation pulse that is applied to the axon 12 in the absence of a depolarizing pre-pulse.

As another example, a relatively long (e.g., 500 μs or more, 1 ms being typical) hyperpolarizing pre-pulse applied to the axon 12 at a relatively low level will initially decrease the percentage of the h-gates 30 that are partially or completely closed without evoking an action potential in the axon 12, thereby activating more sodium ion channels 24. As a result, the action potential threshold of the axon 12 (i.e., the voltage level at which an action potential is evoked in the axon) will be decreased, since the stimulation pulse can activate a lesser percentage of sodium ion channels 24 to evoke an action potential in the axon 12. Thus, a stimulation pulse applied soon after a long hyperpolarizing pre-pulse need not be as strong to evoke the action potential within the axon 12 relative to a stimulation pulse that is applied to the axon 12 in the absence of a hyperpolarizing pre-pulse.

While the use of a relatively long conditioning pulse has been successful in certain applications, a relatively long stimulation pulse (e.g., 500 μs or greater) is required for the long conditioning pulse to be effective. In certain indications, however, relatively short stimulation pulse widths are most effective for achieving therapeutic benefit. For example, clinicians typically use stimulation pulse widths within the range of 60 μs-90 μs when performing DBS of the subthalamic nucleus and DBS of the thalamus. (See The Deep-Brain Stimulation for Parkinson's Disease Study Group, *Deep-Brain Stimulation of the Subthalamic Nucleus or the Pars Interna of the Globus Pallidus in Parkinson's Disease*, N Engl J Med, Vol. 345, No. 13, Sep. 27, 2001). As another example, short duration stimulation pulses advantageously increase the threshold difference between nerve fibers of different diameters, and increase the slope of the current-distance relationship, thereby increasing tissue stimulation selectivity (See *Inversion of the Current-Distance Relationship by Transient Depolarization*, IEEE Transactions on Biomedical Engineering, Vol. 44, No. 1, January 1997). In addition to being much less effective when coupled with short duration stimulation pulses, the use of long duration conditioning pulses increases the "stimulation" period and limits the operable frequency range of the IPG, especially when coupled with interleaved stimulation (e.g., bilateral DBS).

There, thus, remains a need for an improved method and system that conditions tissue for short duration stimulation pulses.

SUMMARY OF THE INVENTION

In accordance with a first aspect of the present inventions, a method of providing therapy to a patient is provided. The method comprises placing at least one electrode in contact with tissue of a patient, conveying a sub-threshold, hyperpolarizing, conditioning pre-pulse (e.g., an anodic pulse) from the electrode(s) to render a first region of the tissue (e.g., dorsal root fibers) less excitable to stimulation, and conveying a depolarizing stimulation pulse (e.g., a cathodic pulse) from the electrode(s) to stimulate a second different region of the tissue (e.g., dorsal column fibers). In one method, the electrode(s) comprises a first electrode and a second electrode, the conditioning pre-pulse is conveyed from the first electrode, and the stimulation pulse is conveyed from the second electrode. An optional method comprises conveying a sub-threshold, hyperpolarizing conditioning post-pulse from the electrode(s) to further render the first tissue region less excitable to stimulation. The conditioning post-pulse may overlap the stimulation pulse in time to create a concurrent pulse.

In accordance with a second aspect of the present inventions, another method of providing therapy to a patient is provided. The method comprises placing at least one electrode in contact with tissue of a patient, conveying a sub-threshold, hyperpolarizing, conditioning pre-pulse (e.g., an anodic pulse) from the at least one electrode to the tissue, and conveying a depolarizing stimulation pulse (e.g. a cathodic pulse) from the electrode to the tissue. The conditioning pre-pulse has a relatively short duration, and in particular, a duration less than 200 μs. In one method, the duration is equal to or less than 150 μs, and can even be equal to or less than 75 μs. In another method, the stimulation pulse has a relatively short duration, and in particular, a duration less than 200 μs. The conditioning pre-pulse and stimulation pulse may be conveyed from separate electrode, and a conditioning post-pulse may be provided, as discussed above.

In accordance with a third aspect of the present inventions, a neurostimulation system is provided. The neurostimulation system comprises a plurality of electrical contacts, and analog output circuitry capable of outputting electrical pulses to the plurality of electrical contacts in accordance with a pulse pattern. The neurostimulation system further comprises control circuitry capable of defining the pulse pattern, such that the electrical pulses comprise a sub-threshold, conditioning, pre-pulse (e.g., an anodic pulse) outputted to a first one of the electrical contacts, and a stimulation pulse (e.g., a cathodic pulse) outputted to a second different one of the electrical contacts. The conditioning pre-pulse has a duration less than 200 μs, and in one embodiment, has a duration equal to or less than 150 μs, or even equal to or less than 75 μs. In one embodiment, the stimulation pre-pulse has a duration less than 200 μs. In another embodiment, the control circuitry is capable of defining the pulse pattern, such that the electrical pulses further comprise a sub-threshold, conditioning, post-pulse outputted to the first electrical contact. The conditioning post-pulse may overlap the stimulation pulse in time to create a conditioning concurrent pulse.

The neurostimulation system may further comprise one or more stimulation leads carrying a plurality of electrodes in electrical communication with the plurality of electrical contacts. For example, in one embodiment, the one or more stimulation leads comprises one or more spinal cord stimulation leads. The neurostimulation system may further comprise a memory capable of storing a set of stimulation parameters, in which case, the control circuitry is capable of defining the pattern in accordance with the stimulation parameter set. The neurostimulation system may further comprise a case, in which case, the plurality of electrical contacts, analog output circuitry, and control circuitry can be contained in the case to form a neurostimulator.

While the present inventions should not be so limited in their broadest aspects, the use of a hyperpolarizing conditioning pre-pulse has been discovered to increase the stimulation threshold of the first tissue region over the stimulation threshold increased by a long duration depolarizing conditioning pre-pulse. In particular, hyperpolarizing, conditioning pre-pulses of relatively short duration predominantly act on the m-gates of axons, in contrast to depolarizing, conditioning pre-pulses of longer duration, which predominantly act on the h-gates of axons. In this manner, the short hyperpolarizing, conditioning pre-pulses can still be effective even when coupled with stimulation pulses of relatively short duration.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG), radio rate (RF) transmitter, or similar electrical stimulator, that may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, a peripheral nerve stimulator, or in any other neural stimulator configured to treat urinary incontinence, sleep apnea, shoulder sublaxation, etc.

Figure 1:
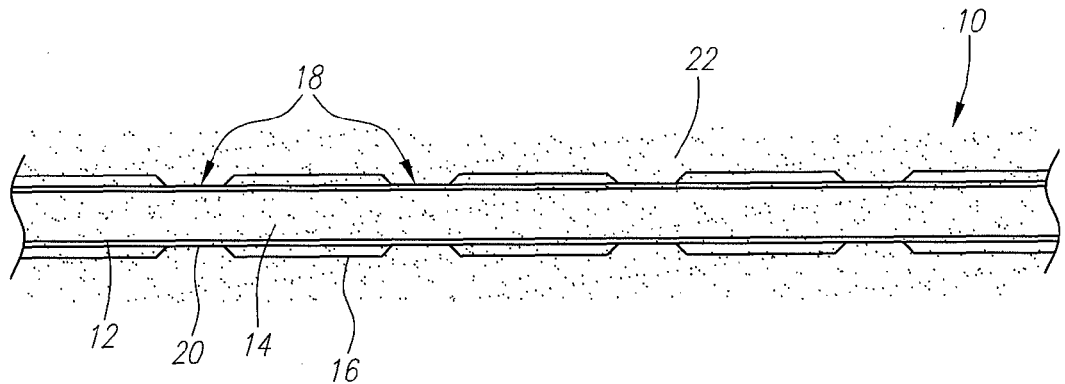
FIG. 1 is a cross-sectional view of a typical neuron.
Figure 2A:
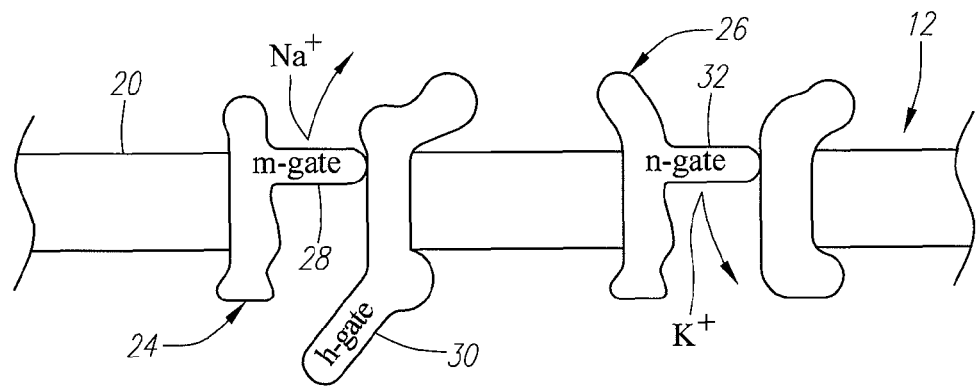
FIGS. 2a-2d are plan views of operation of the gates of the sodium ion channels and potassium ion channels during an action potential evoked within the axon of the neuron of FIG. 1.
Figure 2B:
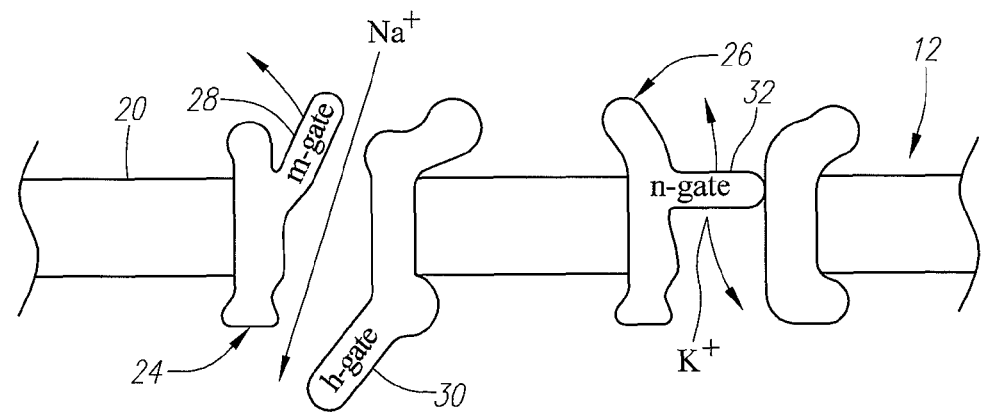
Figure 2C:
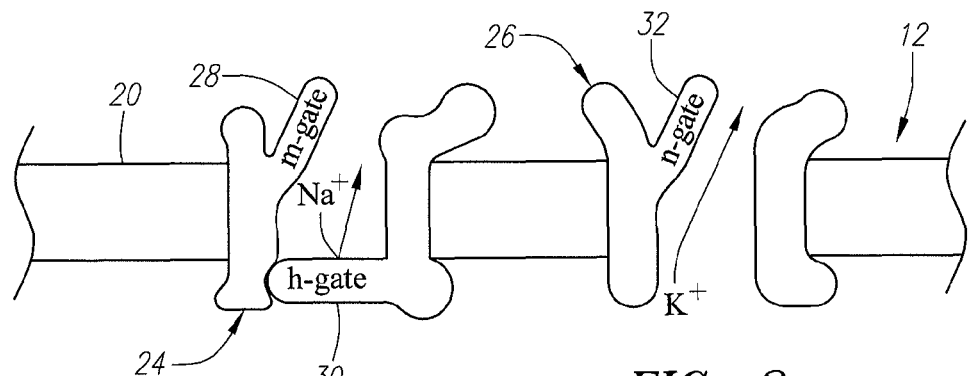
Figure 2D:
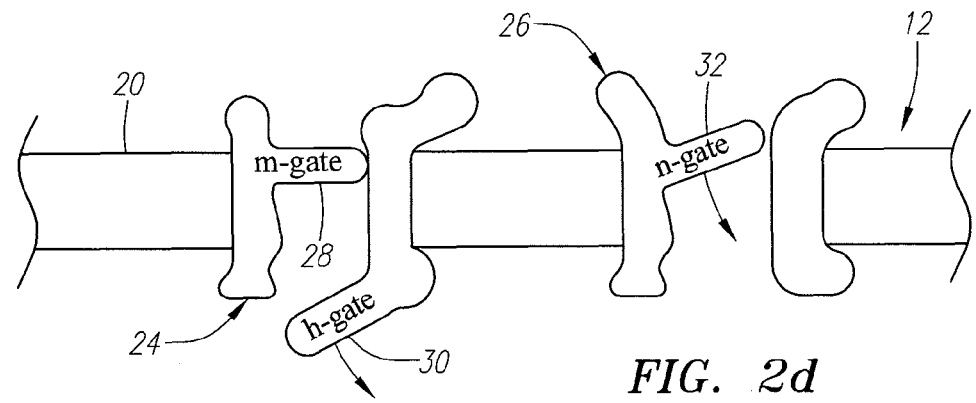
Figure 3:
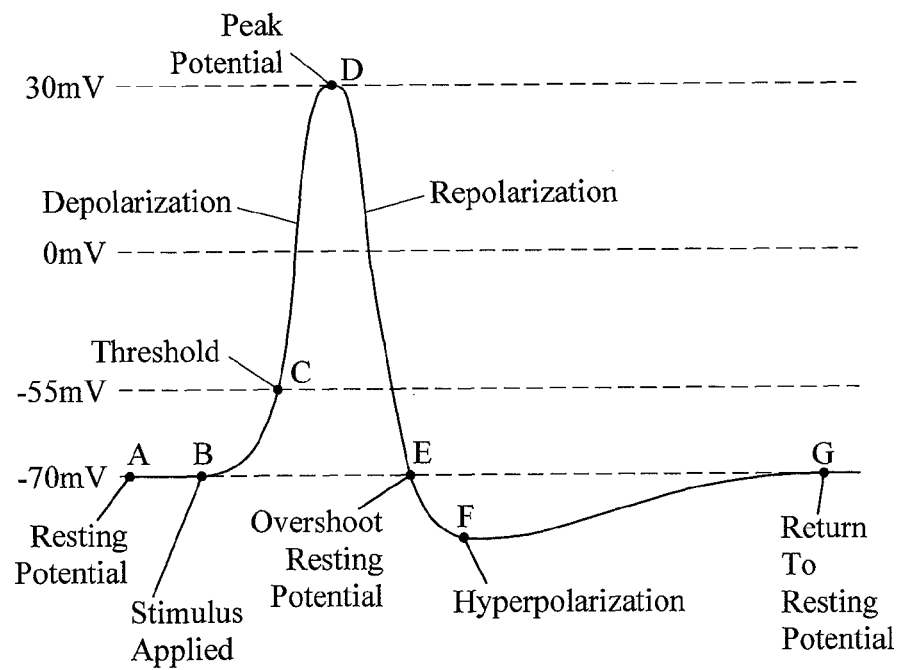
FIG. 3 is a diagram of the transmembrane voltage potential during an action potential evoked within the axon of the neuron of FIG. 1.
Figure 4:
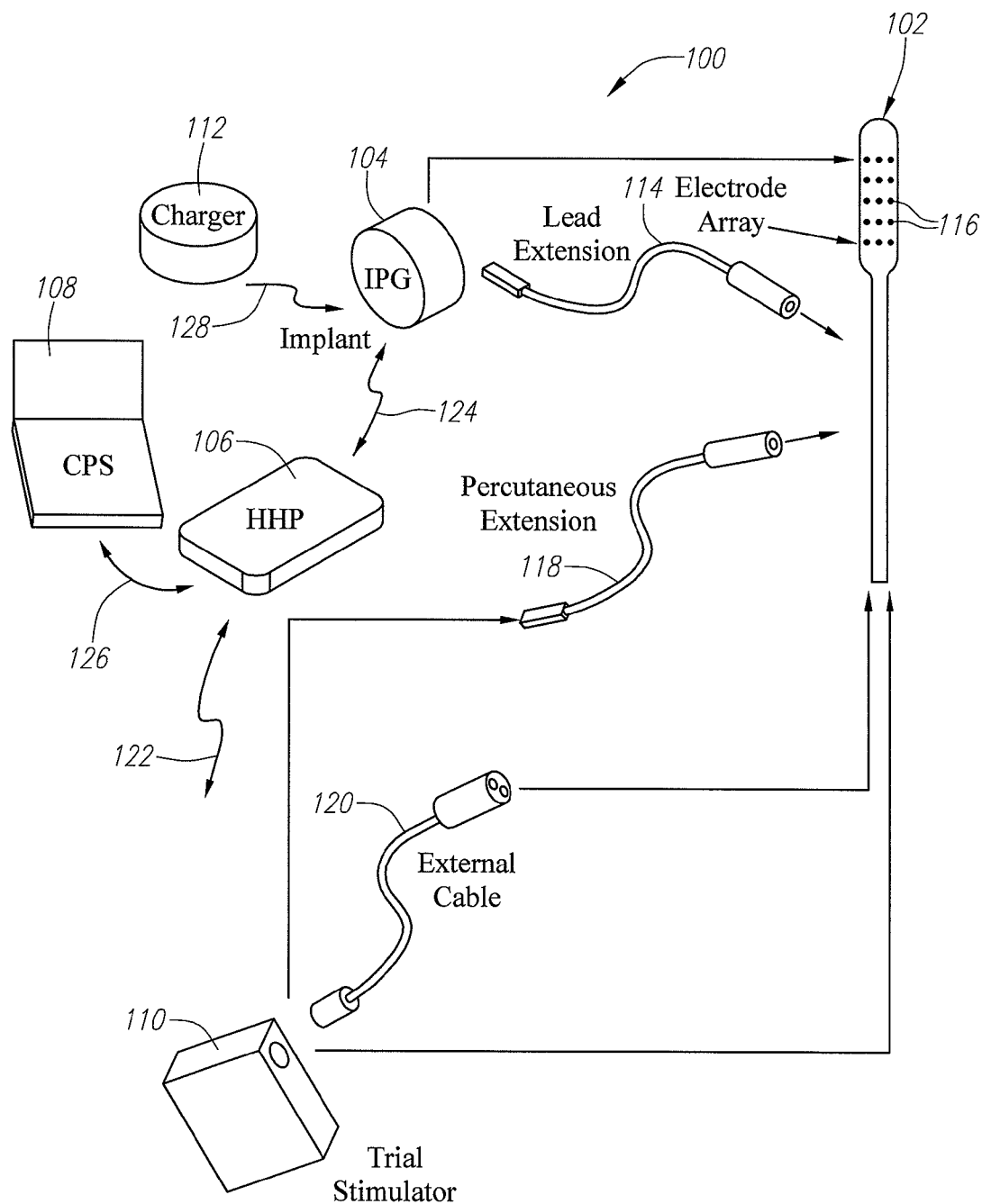
FIG. 4 is plan view of one embodiment of a spinal cord stimulation (SCS) system arranged in accordance with the present inventions.

Turning first to FIG. 4, an exemplary SCS system 100 generally at least one implantable stimulation lead 102, an implantable pulse generator (IPG) 104 (or alternatively RF receiver-stimulator), an external handheld programmer (HHP) 106, a Clinician's Programmer Station (CPS) 108, an External Trial Stimulator (ETS) 110, and an external charger 112.

The IPG 104 is physically connected via a percutaneous lead extension 114 to the stimulation lead 102, which carries an array of electrodes 116. The ETS 110 may also be physically connected via a percutaneous lead extension 118 and external cable 120 to the stimulation lead 102. The ETS 110, which has similar pulse generation circuitry as the IPG 104, also provides electrical stimulation energy to the electrode array 116 in accordance with a set of stimulation parameters. The major difference between the ETS 110 and the IPG 104 is that the ETS 110 is a non-implantable device that is used on a trial basis after the stimulation lead 12 has been implanted and prior to implantation of the IPG 104, to test the effectiveness of the stimulation that is to be provided.

The HHP 106 may be used to telemetrically control the ETS 110 via a bi-directional RF communications link 122. Once the IPG 104 and stimulation lead 102 are implanted, the HHP 106 may be used to telemetrically control the IPG 104 via a bi-directional RF communications link 124. Such control allows the IPG 104 to be turned on or off and to be programmed with different stimulation programs after implantation. Once the IPG 104 has been programmed, and its power source has been charged or otherwise replenished, the IPG 104 may function as programmed without the HHP 106 being present.

The CPS 108 provides clinician detailed stimulation parameters for programming the IPG 104 and ETS 110 in the operating room and in follow-up sessions. The CPS 108 may perform this function by indirectly communicating with the IPG 104 or ETS 110, through the HHP 106, via an IR communications link 126. Alternatively, the CPS 108 may directly communicate with the IPG 104 or ETS 110 via an RF communications link (not shown). The external charger 112 is a portable device used to transcutaneously charge the IPG 104 via an inductive link 128.

For purposes of brevity, the details of the HHP 106, CPS 108, ETS 110, and external charger 112 will not be described herein. Details of exemplary embodiments of these devices are disclosed in U.S. Pat. No. 6,895,280, which is expressly incorporated herein by reference.

Figure 5:
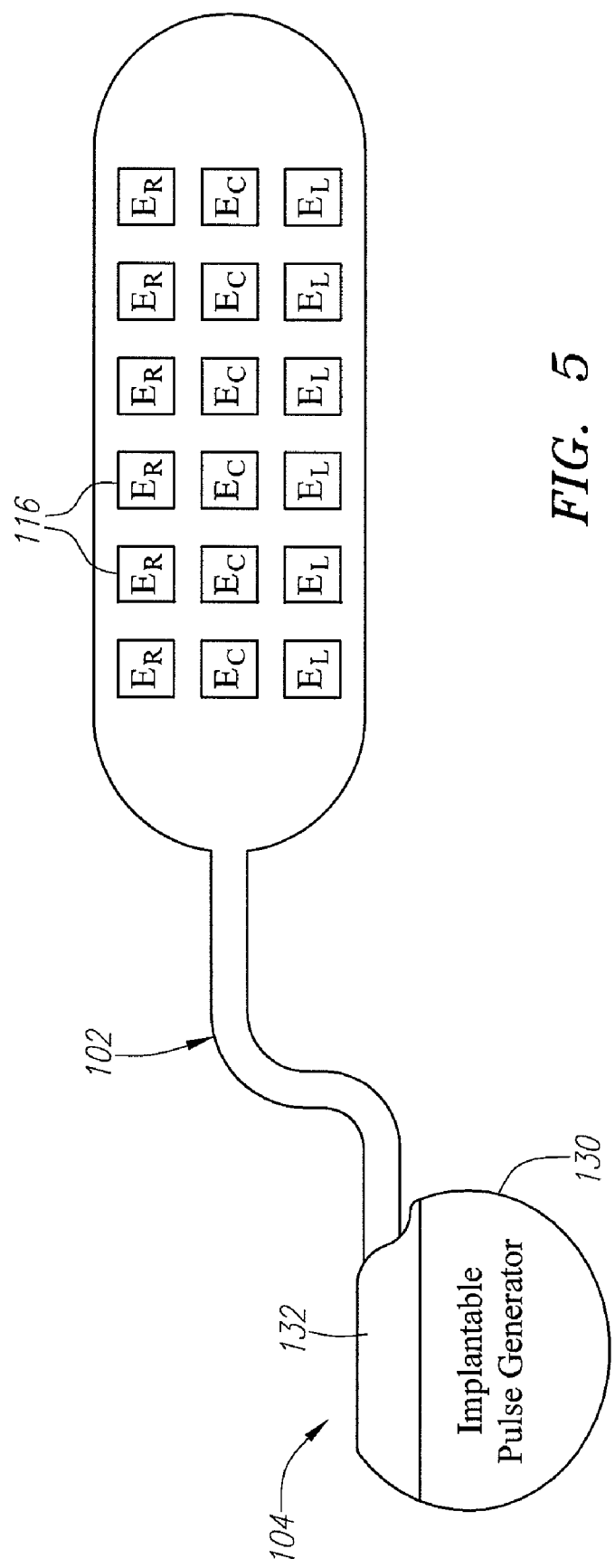
FIG. 5 is a plan view of an implantable pulse generator (IPG) and stimulation lead used in the SCS system of FIG. 4.

Referring further to FIG. 5, the IPG 104 comprises an outer case 130 for housing the electronic and other components (described in further detail below), and a connector 132 in which the proximal end of the stimulation lead 102 mates in a manner that electrically couples the electrodes 116 to the electronics within the outer case 130. The outer case 130 is composed of an electrically conductive, biocompatible material, such as titanium, and forms a hermetically sealed compartment wherein the internal electronics are protected from the body tissue and fluids. In some cases, the outer case 130 serves as an electrode.

In the illustrated embodiment, the stimulation lead 102 is a paddle lead having a flat paddle-shaped distal end, wherein the electrodes 116 are carried on one side of the paddle. The electrodes 116 are arranged in three columns along the axis of the stimulation lead 102, with the electrodes in one lateral column (left column when lead 102 is introduced into the patient in the rostral direction) being labeled $E_L$, the electrodes in the center column being labeled $E_C$, and the electrodes in the other lateral column (right column when lead 102 is introduced into the patient in the rostral direction) being labeled $E_R$. Each row of the electrodes 116 (which includes a left electrode $E_L$, a center electrode $E_C$, and a right electrode $E_R$) is arranged in a line transversely to the axis of the lead 102. The actual number of leads and electrodes will, of course, vary according to the intended application. In alternative embodiments, one or more percutaneous leads with electrodes arranged in-line along the leads can be provided.

As will be described in further detail below, the IPG 104 includes pulse generation circuitry that provides electrical conditioning and stimulation energy to the electrode array 116 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 104 supplies constant current or constant voltage to the electrode array 116), pulse duration (measured in microseconds), pulse rate (measured in pulses per second), and delay between stimulation and conditioning pulses (measured in microseconds).

With respect to the pulse patterns provided during operation of the SCS system 100, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case, so that the electrical current has a path from the energy source contained within the IPG case to the tissue and a return path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 116 is activated along with the case of the IPG 104, so that electrical energy is transmitted between the selected electrode 116 and case. Monopolar delivery may also occur when one or more of the lead electrodes 116 are activated along with a large group of lead electrodes 116 located remotely from the one more lead electrodes 116 so as to create a monopolar effect; that is, electrical energy is conveyed from the one or more lead electrodes 116 in a relatively isotropic manner.

Bipolar delivery occurs when two of the lead electrodes 116 are activated as anode and cathode, so that electrical energy is transmitted between the selected electrodes 116. For example, the center electrode $E_C$ may be activated as an anode at the same time that the left electrode $E_L$ is activated as a cathode. Tripolar delivery occurs when three of the lead electrodes 116 are activated, two as anodes and the remaining one as a cathode, or two as cathodes and the remaining one as an anode. For example, the left and right electrodes $E_L$, $E_R$ may be activated as anodes at the same time that the center electrode $E_C$ is activated as a cathode.

Figure 6:
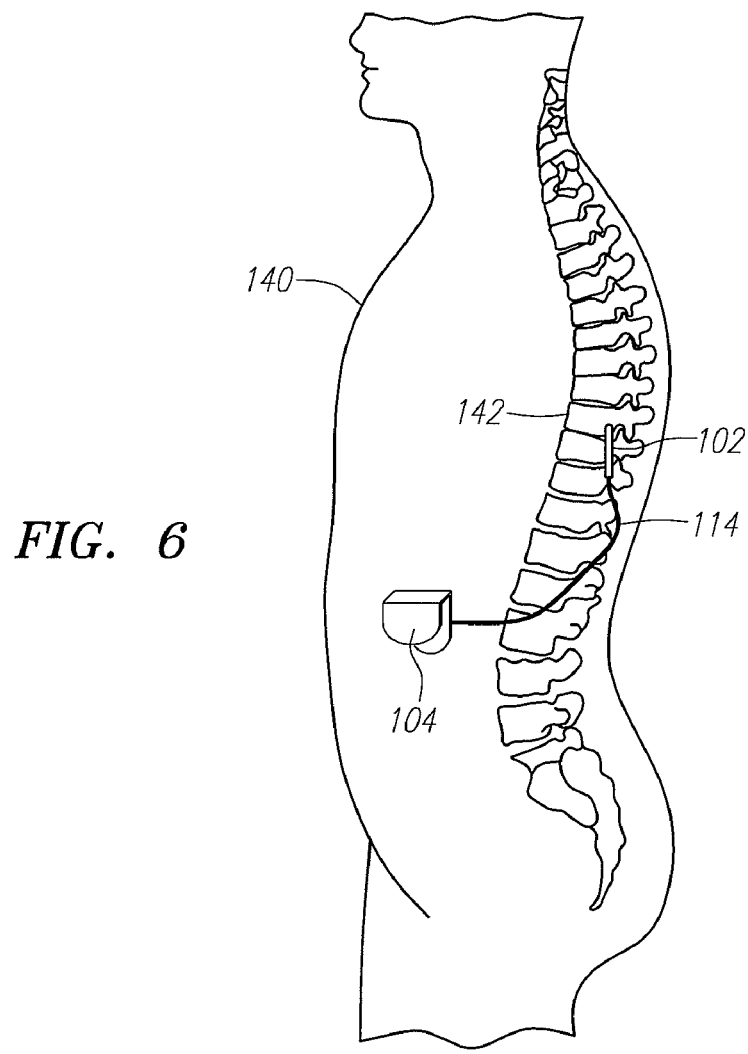
FIG. 6 is a plan view of the SCS system of FIG. 4 in use with a patient.

Referring to FIG. 6, the stimulation lead 102 is implanted within the spinal column 142 of a patient 140. The preferred placement of the stimulation lead 102 is adjacent, i.e., resting upon, the spinal cord area to be stimulated. Due to the lack of space near the location where the stimulation lead 102 exits the spinal column 140, the IPG 104 is generally implanted in a surgically-made pocket either in the abdomen or above the buttocks. The IPG 104 may, of course, also be implanted in other locations of the patient's body. The lead extension 114 facilitates locating the IPG 104 away from the exit point of the stimulation lead 102. After implantation, the IPG 104 is used to provide the therapeutic stimulation under control of the patient.

Figure 7:
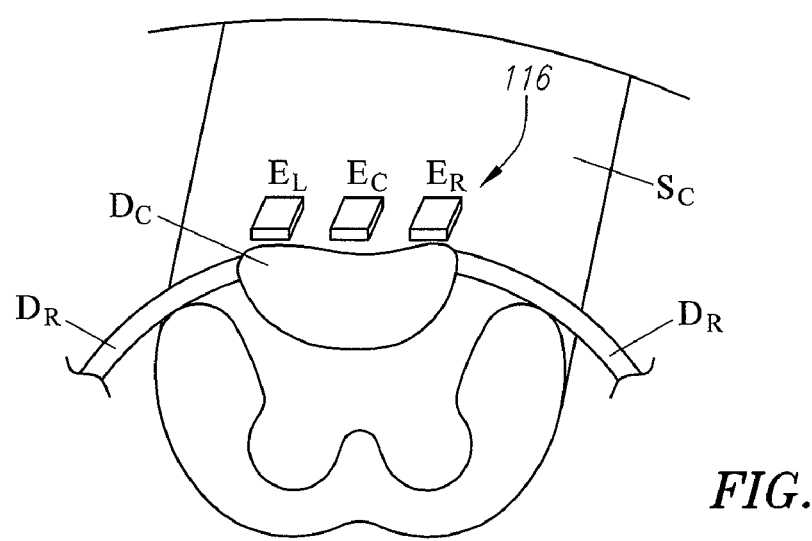
FIG. 7 is a perspective view of one row of electrodes of the stimulation lead of FIG. 5 is contact with a spinal cord.

As shown in FIG. 7, a row of electrodes 116 are arranged along a line transverse to the axis of the spinal cord SC, such that the center electrode $E_C$ is located over the center of the dorsal column (DC) nerve fibers, and the left and right electrodes $E_L$, $E_R$ are laterally placed from the center of the DC nerve fibers adjacent the respective dorsal root (DR) nerve fibers, thereby forming a medio-lateral electrode configuration. Alternatively, if a percutaneous stimulation lead is used, the electrodes of the lead can be arranged in a line along the axis of the spinal cord SC, or if multiple percutaneous stimulation leads are used, the electrodes may be arranged in unstaggered columns, such that a row of electrodes may be placed in contact with the spinal cord SC in the manner shown in FIG. 7. In a case where only two columns of electrodes are provided, one column of electrodes can be placed laterally on one side of the centerline of the spinal cord SC and the other column of electrodes can be placed laterally on the other side of the centerline of the spinal cord SC. In alternative embodiments, electrodes may be rostro-caudally arranged in a line parallel to the axis of the spinal cord SC.

Figure 8:
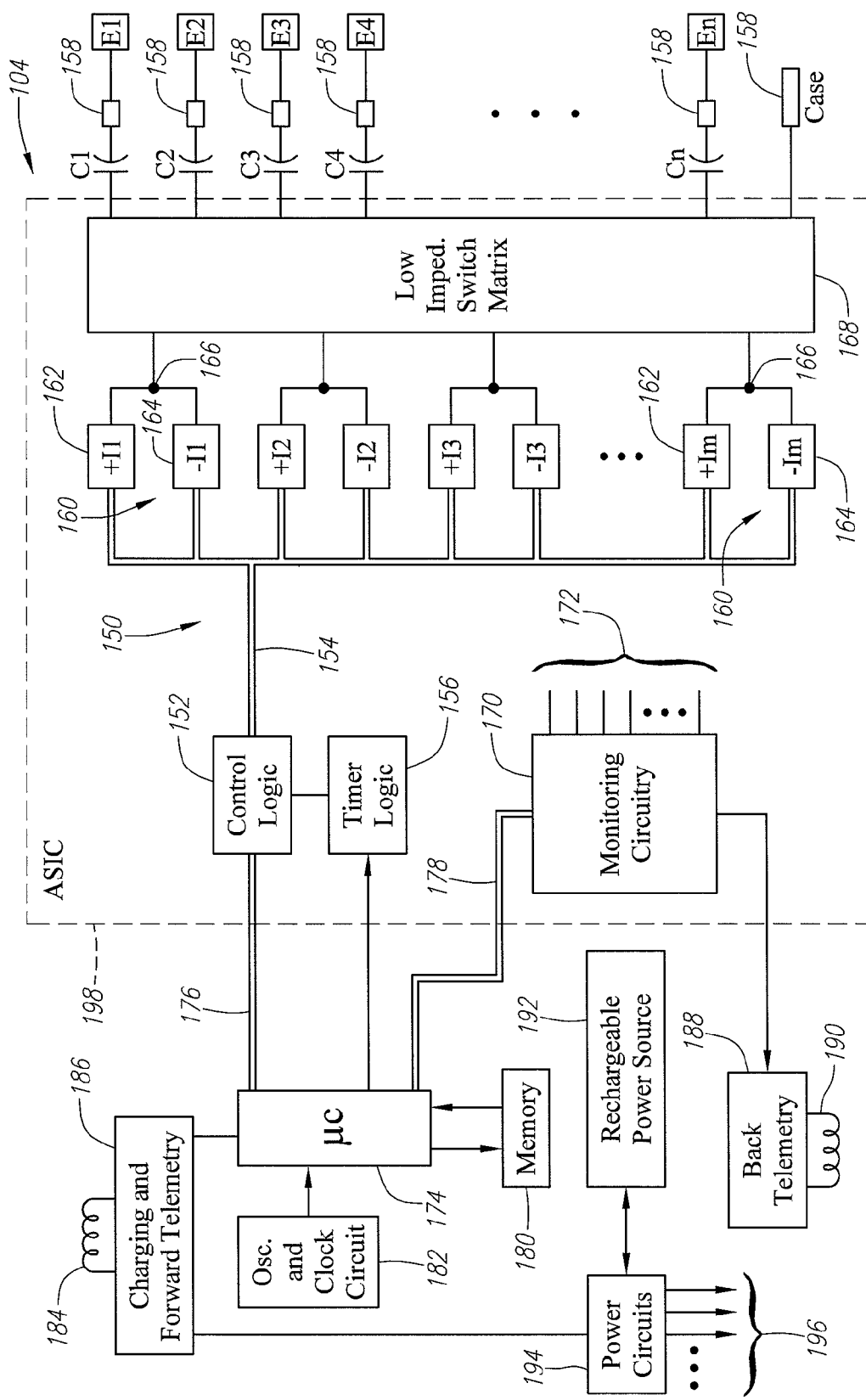
FIG. 8 is a block diagram of the internal components of the IPG of FIG. 5.

Turning next to FIG. 8, the main internal components of the IPG 104 will now be described. The IPG 104 includes analog output circuitry 150 capable of individually generating electrical pulses of specified amplitude under control of control logic 152 over data bus 154. The pulse rate and pulse width of the electrical pulses output by the IPG 104 are controlled using the timer logic circuitry 156. The timer logic circuitry 156 may have a suitable resolution, e.g., 10 µs. These electrical pulses are supplied via capacitors C1-Cn to electrical contacts 158 corresponding to electrodes E1-En and the case electrode. As will be described in further detail below, the analog output circuitry 150 is capable of outputting both sub-threshold conditioning pulses and stimulation pulses to the electrical contacts 158, and thus, the electrodes E1-En.

In the illustrated embodiment, the analog output circuitry 150 comprises a plurality m independent current source pairs 160 capable of supplying electrical energy to the electrical contacts 158 at a specified and known amperage. One current source 162 of each pair 160 functions as a positive (+) or anodic current source, while the other current source 164 of each pair 160 functions as a negative (−) or cathodic current source. The outputs of the anodic current source 162 and the cathodic current source 164 of each pair 160 are connected to a common node 166. The analog output circuitry 150 further comprises a low impedance switching matrix 168 through which the common node 166 of each current source pair 160 is connected to any of the electrical contacts 158 via the capacitors C1-Cn. Alternatively, the analog output circuitry 150 does not use a low impedance switching matrix 168, but rather uses a bidirectional current source for each of the electrical contacts 158.

Thus, for example, it is possible to program the first anodic current source 162 (+I1) to produce a pulse of +4 ma (at a specified rate and for a specified duration), and to synchronously program the second cathodic current source 164 (−I2) to similarly produce a pulse of −4 ma (at the same rate and pulse width), and then connect the node 86 of the anodic current source 162 (+I1) to the electrical contact 158 corresponding to electrode E3, and connect the node 80 of the cathodic current source 164 (−I2) to the electrical contact 158 corresponding to electrode E1.

Hence, it is seen that each of the programmable electrical contacts 158 can be programmed to have a positive (sourcing current), a negative (sinking current), or off (no current) polarity. Further, the amplitude of the current pulse being sourced or sunk from a given electrical contact 158 may be programmed to one of several discrete levels. In one embodiment, the current through each electrical contact 158 can be individually set from 0 to ±10 ma in steps of 100 μa, within the output voltage/current requirements of the IPG 104. Additionally, in one embodiment, the total current output by a group of electrical contacts 158 can be up to ±20 ma (distributed among the electrodes included in the group). Moreover, it is seen that each of the electrical contacts 158 can operate in a multipolar mode, e.g., where two or more electrical contacts are grouped to source/sink current at the same time. Alternatively, each of the electrical contacts 158 can operate in a monopolar mode where, e.g., the electrical contacts 158 are configured as cathodes (negative), and case of the IPG 104 is configured as an anode (positive).

It can be appreciated that an electrical contact 158 may be assigned an amplitude and included with any of up to k possible groups, where k is an integer corresponding to the number of channels, and in preferred embodiment is equal to 4, and with each channel k having a defined pulse width and pulse rate. Other channels may be realized in a similar manner. Thus, each channel identifies which electrical contacts 158 (and thus electrodes) are selected to synchronously source or sink current, the pulse amplitude at each of these electrical contacts, and the pulse width and pulse rate.

In an alternative embodiment, rather than using independently controlled current sources, independently controlled voltage sources for providing electrical pulses of a specified and known voltage at the electrical contacts 158 can be provided. The operation of this output circuitry, including alternative embodiments of suitable output circuitry for performing the same function of generating electrical pulses of a prescribed amplitude and width, is described more fully in U.S. Pat. Nos. 6,516,227 and 6,993,384, which are expressly incorporated herein by reference.

The IPG 104 further comprises monitoring circuitry 170 for monitoring the status of various nodes or other points 172 throughout the IPG 104, e.g., power supply voltages, temperature, battery voltage, and the like. The IPG 104 further comprises processing circuitry in the form of a microcontroller 174 that controls the control logic 152 over data bus 176, and obtains status data from the monitoring circuitry 170 via data bus 178. The IPG 104 additionally controls the timer logic 156. The IPG 104 further comprises memory 180 and oscillator and clock circuit 182 coupled to the microcontroller 174. The microcontroller 174, in combination with the memory 180 and oscillator and clock circuit 182, thus comprise a microprocessor system that carries out a program function in accordance with a suitable program stored in the memory 180. Alternatively, for some applications, the function provided by the microprocessor system may be carried out by a suitable state machine.

Thus, the microcontroller 174 generates the necessary control and status signals, which allow the microcontroller 174 to control the operation of the IPG 104 in accordance with a selected operating program and electrical stimulation parameters. In controlling the operation of the IPG 104, the microcontroller 174 is able to individually generate electrical pulses at the electrodes 116 using the analog output circuitry 150, in combination with the control logic 152 and timer logic 156, thereby allowing each electrode 116 to be paired or grouped with other electrodes 116, including the monopolar case electrode, and to control the polarity, amplitude, rate, pulse width, delay between conditioning pre-pulses and stimulation pulses, and channel through which the current stimulus pulses are provided.

The IPG 104 further comprises an alternating current (AC) receiving coil 184 for receiving programming data (e.g., the operating program and/or stimulation parameters) from the HHP 106 in an appropriate modulated carrier signal, and charging and forward telemetry circuitry 186 for demodulating the carrier signal it receives through the AC receiving coil 184 to recover the programming data, which programming data is then stored within the memory 180, or within other memory elements (not shown) distributed throughout the IPG 104.

The IPG 104 further comprises back telemetry circuitry 188 and an alternating current (AC) transmission coil 190 for sending informational data sensed through the monitoring circuitry 170 to the HHP 106. The back telemetry features of the IPG 104 also allow its status to be checked. For example, any changes made to the stimulation parameters are confirmed through back telemetry, thereby assuring that such changes have been correctly received and implemented within the IPG 104. Moreover, upon interrogation by the HHP 106, all programmable settings stored within the IPG 104 may be uploaded to the HHP 106.

The IPG 104 further comprises a rechargeable power source 192 and power circuits 194 for providing the operating power to the IPG 104. The rechargeable power source 192 may, e.g., comprise a lithium-ion or lithium-ion polymer battery. The rechargeable battery 192 provides an unregulated voltage to the power circuits 194. The power circuits 194, in turn, generate the various voltages 196, some of which are regulated and some of which are not, as needed by the various circuits located within the IPG 104. The rechargeable power source 192 is recharged using rectified AC power (or DC power converted from AC power through other means, e.g., efficient AC-to-DC converter circuits, also known as "inverter circuits") received by the AC receiving coil 184. To recharge the power source 192, an external charger (not shown), which generates the AC magnetic field, is placed against, or otherwise adjacent, to the patient's skin over the implanted IPG 104. The AC magnetic field emitted by the external charger induces AC currents in the AC receiving coil 184. The charging and forward telemetry circuitry 186 rectifies the AC current to produce DC current, which is used to charge the power source 192. While the AC receiving coil 184 is described as being used for both wirelessly receiving communications (e.g., programming and control data) and charging energy from the external device, it should be appreciated that the AC receiving coil 184 can be arranged as a dedicated charging coil, while another coil, such as coil 190, can be used for bi-directional telemetry.

As shown in FIG. 8, much of the circuitry included within the IPG 104 may be realized on a single application specific integrated circuit (ASIC) 198. This allows the overall size of the IPG 104 to be quite small, and readily housed within a suitable hermetically-sealed case. Alternatively, most of the circuitry included within the IPG 104 may be located on multiple digital and analog dies, as described in U.S. patent application Ser. No. 11/177,503, filed Jul. 8, 2005, which is incorporated herein by reference in its entirety. For example, a processor chip, such as an application specific integrated circuit (ASIC), can be provided to perform the processing functions with on-board software. An analog IC (AIC) can be provided to perform several tasks necessary for the functionality of the IPG 104, including providing power regulation, stimulus output, impedance measurement and monitoring. A digital IC (DigIC) may be provided to function as the primary interface between the processor IC and analog IC by controlling and changing the levels and sequences of the current output by the stimulation circuitry in the analog IC when prompted by the processor IC.

It should be noted that the diagram of FIG. 8 is functional only, and is not intended to be limiting. Those of skill in the art, given the descriptions presented herein, should be able to readily fashion numerous types of IPG circuits, or equivalent circuits, that carry out the functions indicated and described. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 100 may alternatively utilize an implantable receiver-stimulator (not shown) connected to the stimulation lead 102. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above, the IPG 104 (or ETS 110) is capable of outputting both conditioning pulses and stimulation pulses to the electrical contacts 158, and thus, the electrodes 116 and case electrode. Using the electrode arrangement illustrated in FIG. 7, the IPG 104 (or ETS 110) preferentially stimulates a tissue region relative to another tissue region, and in the illustrated case, preferentially stimulates the DC nerve fibers, while suppressing stimulation of the DR nerve fibers. In particular, the DR nerve fibers are rendered less excitable to a subsequent electrical pulse by conveying a sub-threshold conditioning pre-pulse from left and right electrodes $E_L$, $E_R$, and the DC nerve fibers are subsequently stimulated by conveying a stimulation pulse from the center electrode $E_c$. Alternatively, the IPG 104 (or ETS 110) preferentially stimulates the DR nerve fibers, while suppressing stimulation of the DC nerve fibers. In particular, the DC nerve fibers are rendered less excitable to a subsequent electrical pulse by conveying a sub-threshold conditioning pre-pulse from the center electrode $E_c$, and the DR nerve fibers are subsequently stimulated by conveying stimulation pulses from left and right electrodes $E_L$, $E_R$. Any either event, the conditioning pulses and stimulation pulses may be delivered to the electrodes in a monopolar manner, a bipolar manner, or both, as described in U.S. patent application Ser. No. 11/752,898, which is expressly incorporated herein by reference.

Notably, in the SCS context, the electrodes 116 are placed as closely as possible to the neural tissue of the spinal cord in order to maximize the resolution of the energy transmitted by the electrodes 116; that is, to focus the stimulating effect of the stimulation pulses on the tissue intended to be stimulated, and to focus the suppressing effect of the sub-threshold conditioning pulses on the tissue intended to be suppressed. Preferably, the proximity of the electrodes to the neural tissue should be less than one-half of the distance between adjacent electrodes to ensure the proper resolution. Because the electrodes 116 are typically separated from the neural tissue by the dura and spinal cord fluid, there will typically be some distance between the electrodes 116 and the neural tissue, with the distance varying from patient to patient. If implanted within the cervical region of the spine, the proximity of the electrodes to the neural tissue will typically be quite small, and therefore, high resolution can be achieved. If implanted within the thoracic region of the spine, the proximity of the electrodes to the neural tissue will be greater, and therefore, a lower resolution will be achieved.

Figure 9:
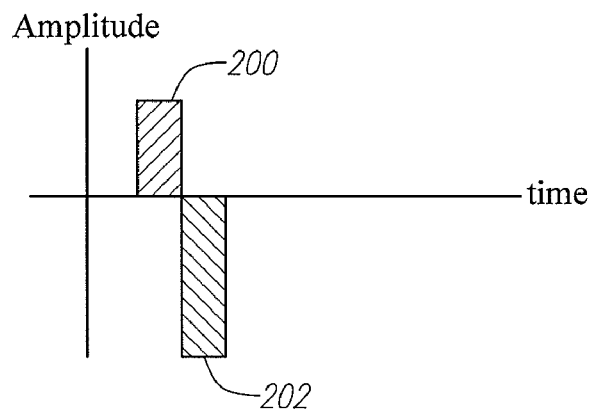
FIG. 9 is a diagram of one waveform that can be generated by the IPG of FIG. 8, wherein the waveform comprises a sub-threshold, anodic, conditioning pre-pulse and a cathodic stimulation pulse.

In one embodiment illustrated in FIG. 9, each conditioning pulse takes the form of a sub-threshold, anodic, conditioning pre-pulse 200, which serves to hyperpolarize tissue to render it less excitable to subsequent stimulation, and the stimulation pulse takes the form of a cathodic stimulation pulse 202 that serves to depolarize the tissue to evoke an action potential. Notably, as the duration between the conditioning pulse 200 and the stimulation pulse 202 decreases, the effect of the conditioning pulse 200 increases. As such, the duration between conditioning pulse 200 and stimulation pulse 202 is preferably zero, but at the least should be less than 100 μs, and more preferably, less than 30 μs.

Significantly, the conditioning pre-pulse 200 has a relatively short duration, preferably less than 200 μs, more preferably less than 150 μs, and most preferably less than 75 μs. As will be described in further detail below, the conditioning pre-pulse 200 is most effective when coupled with a relatively short duration stimulation pulse 202 (e.g., a stimulation pulse having a duration less than 200 μs). In particular, in contrast to prior art tissue conditioning techniques that utilize relatively long depolarizing pre-pulses that act predominantly on the h-gates of the sodium ion channels in the neural axons (by closing the h-gates), the use of relatively short hyperpolarizing pre-pulses act predominantly on the m-gates of the sodium ion channels in the neural axons (by closing the m-gates) to render the tissue less excitable to subsequent stimulation.

Because the conditioning pre-pulse 200 is hyperpolarizing, it also acts to open the h-gates of the sodium ion channels, but to a lesser extent since the h-gates react more slowly than to the m-gates. That is, the relatively short duration of the hyperpolarizing pre-pulse 200 takes advantage of the different time constants of the fast m-gates and the slow h-gates to predominantly act on the m-gates. Thus, unlike the longer duration hyperpolarizing pre-pulses used in prior art techniques, which served to render the tissue more excitable by opening the h-gates, the relatively short duration of the hyperpolarizing pre-pulse 200 serves to render the tissue less excitable by closing the m-gates.

Figure 10:
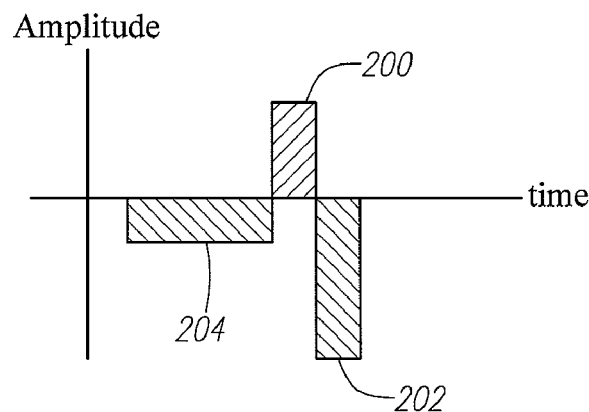
FIG. 10 is a diagram of another waveform that can be generated by the IPG of FIG. 8, wherein the waveform comprises a sub-threshold, cathodic, conditioning pre-pulse, a sub-threshold, anodic, conditioning pre-pulse, and a cathodic stimulation pulse.

In an optional embodiment illustrated in FIG. 10, a relatively long cathodic, conditioning, pre-pulse 204, which serves to depolarize tissue to render it less excitable to the subsequent stimulation pulse 202, precedes the short hyperpolarizing, conditioning, pre-pulse 200. In this case, the long depolarizing, conditioning pre-pulse 204 operates to close the h-gates, in addition to closing of the m-gates by the short hyperpolarizing, conditioning pre-pulse 200, thereby rendering the tissue even less excitable.

Figure 11:
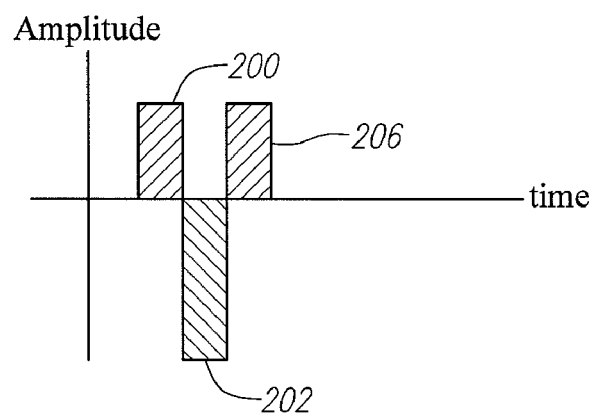
FIG. 11 is a diagram of still another waveform that can be generated by the IPG of FIG. 8, wherein the waveform comprises a sub-threshold, anodic, conditioning pre-pulse, a cathodic stimulation pulse, and a sub-threshold, anodic, conditioning post-pulse.

In another optional embodiment illustrated in FIG. 11, an anodic, conditioning post-pulse 206, which serves to hyperpolarize tissue, follows the stimulation pulse 202, thereby rendering the tissue even less excitable to the stimulation, with the effect of the conditioning post-pulse 206 increasing as the time delay between the stimulation pulse 202 and the conditioning post-pulse 206 approaches zero, preferably within 50 μs. In still another optional embodiment, an anodic, concurrent-pulse (not shown), which serves to further render the tissue less excitable to stimulation, is created. For example, the conditioning post-pulse 206 may overlap the stimulation pulse 202 in time to create the concurrent-pulse, which serves to change the field to avoid stimulation in a local region adjacent the concurrent-pulse. Or a concurrent-pulse distinct from, and having a different amplitude level than, the conditioning post-pulse 206 can be created. In either scenario, it is preferred that the pulses be supplied by independent current or voltage sources to allow the stimulation pulse 202 and post-pulse 206 to be simultaneously created.

Notably, in any of the optional embodiments, if the hyperpolarizing conditioning pre-pulse 202 and stimulation pulse 204 are delivered to two different tissue regions via separate electrodes (e.g., in the manner described with respect to the DR nerve fibers and DC nerve fibers illustrated in FIG. 7), the depolarizing conditioning pre-pulse 204 and the hyperpolarizing conditioning post-pulse 206 are applied to the same tissue region as the hyperpolarizing pre-pulse 202.

For example, the hyperpolarizing conditioning pre-pulse 200, along with the optional depolarizing conditioning pre-pulse 204 and hyperpolarizing conditioning post-pulse 206, can be conveyed from the left and right electrodes $E_L$, $E_R$ to render the DR nerve fibers less excitable to simulation, and the stimulation pulse 202 can be conveyed from the center electrode $E_C$ to stimulate the DC nerve fibers. Or, the hyperpolarizing conditioning pre-pulse 200, along with the optional depolarizing conditioning pre-pulse 204 and hyperpolarizing conditioning post-pulse 206, can be conveyed from the center electrode $E_C$ to render the DC nerve fibers less excitable to simulation, and the stimulation pulse 202 can be conveyed from the left and right electrodes $E_L$, $E_R$ to stimulate the DR nerve fibers.

Figure 12:
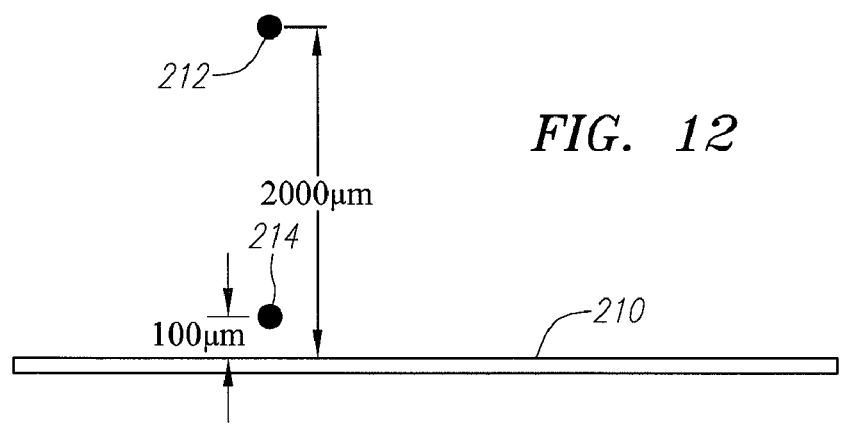
FIG. 12 is a plan view of two electrode point sources adjacent a nerve axon that can be modeled to determine the action potential effect of electrical energy conveyed from the point sources to the nerve axon.

Referring to FIG. 12, a computational model of a neural axon 210, a stimulation electrode 212 that is presumably near a first tissue region that when stimulated yields a therapeutic effect, and a suppression electrode 214 that is presumably near a second tissue region that when stimulate yields undesirable side effects, was generated to perform various case studies described below. Thus, in this scenario, the neural axon 210 represents the second tissue region that yields the side effect when stimulated, and on which the suppression electrode 214 is used to inhibit stimulation evoked by the activity of the stimulation electrode 212. The model of the neural axon 210 is an electrical network model with non-linear dynamics and a diameter of 10 μm. The stimulation and suppression electrodes 212, 214 are modeled as point sources respectively located 2000 μm and 100 μm from the neural axon 210. Of course, other more sophisticated models that include more orientations of nerve fibers, inhomogenous media, and finite sized electrodes, can be used.

Referring to FIGS. 13a-13f, a first case study was conducted by first applying a stimulation pulse to the stimulation electrode 212 alone (i.e., without applying a sub-threshold conditioning pre-pulse to the suppression electrode 214) to determine the amplitude level of the stimulation pulse needed to evoke an action potential in the neural axon 210, and then applying the same stimulation pulse to the stimulation electrode 212 coupled with a sub-threshold, depolarizing, conditioning pre-pulse to the suppression electrode 214 in a prior art manner to determine the amplitude level of the stimulation pulse needed to evoke an action potential in the neural axon 210, and ultimately, to determine the increase in the action potential threshold provided by the depolarizing conditioning pre-pulse as a measure of its inhibitory effect. In this case study, both the conditioning pre-pulse and the stimulation pulse are cathodic, the stimulation pulse was selected to have a duration of 500 μs, the conditioning pre-pulse was selected to have a duration of 1000 μs and an amplitude level of −2.9 μA, and the delay between the conditioning pre-pulse and stimulation pulse was selected to be zero.

Figure 13A:
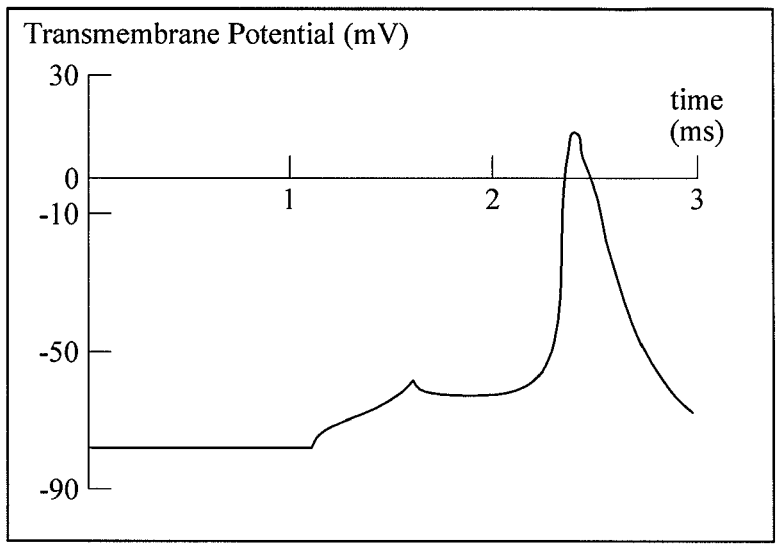
FIGS. 13a-13f are various diagrams illustrating a first case study performed by stimulating the nerve axon of FIG. 12 with a long duration stimulation pulse, alone, and coupled with a long duration, sub-threshold, depolarizing, conditioning pre-pulse.
Figure 13B:
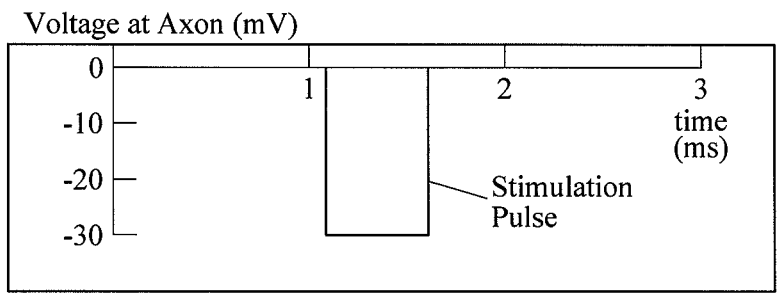
Figure 13C:
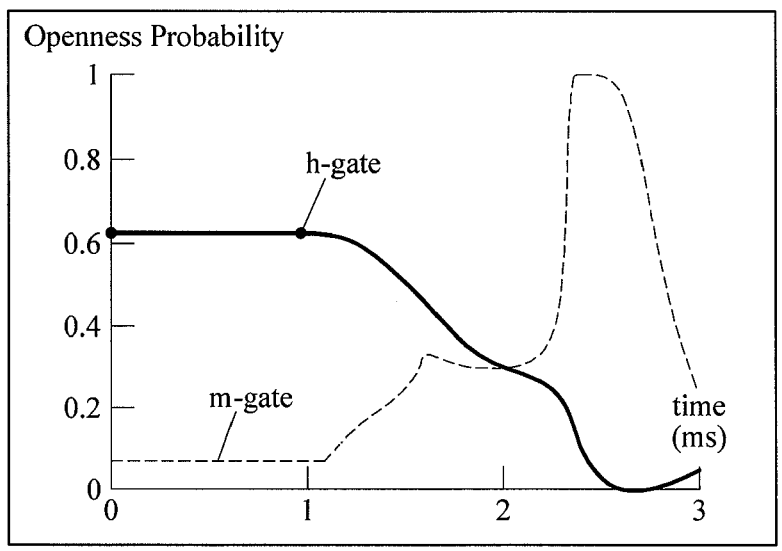

When applied alone, as shown in FIG. 13b, the stimulation pulse was increased from an initial level until an action potential, as represented by the transmembrane voltage in FIG. 13a, was evoked in the neural axon 210. An action potential was found to occur when the amplitude of the stimulation pulse reached −156 μA. Notably, as shown in FIG. 13c, up until the stimulation pulse is applied (when the neural axon 210 is at rest), the probability of any one m-gate being open ("m-gate openness probability") is maintained at a very low level, and the probability of any one h-gate being open ("h-gate openness probability") is maintained at a relatively high level, so that the neural axon 210 is nominally excitable to the subsequent stimulation pulse.

Figure 13D:
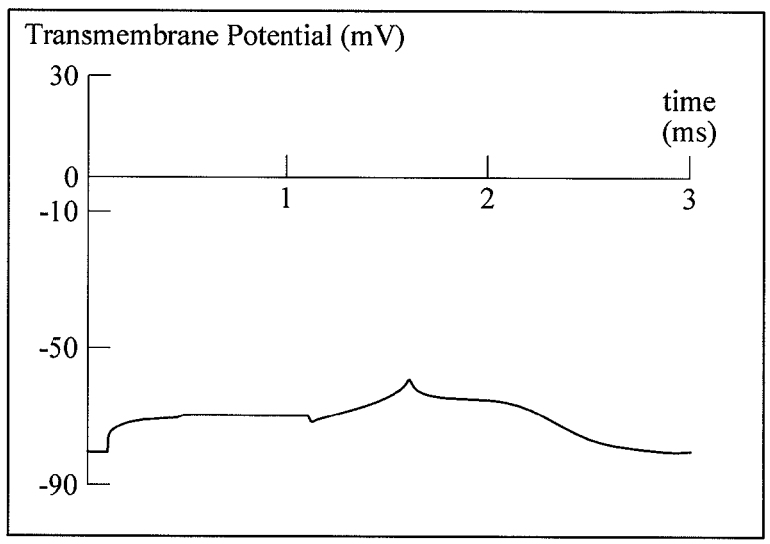
Figure 13E:
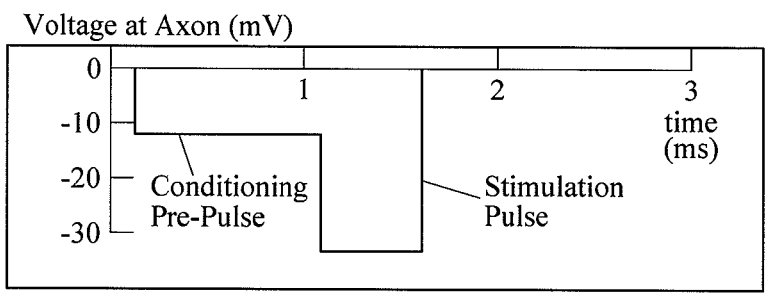
Figure 13F:
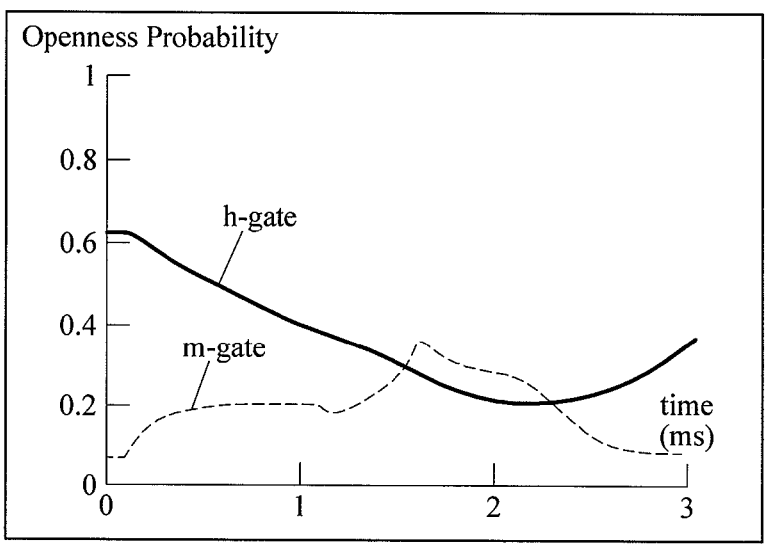

In contrast, when coupled with a depolarizing conditioning pre-pulse, as shown in FIG. 13e, the amplitude of the stimulation pulse was increased from an initial level until an action potential was evoked in the neural axon 210. An action potential was found to occur when the amplitude of the stimulation pulse reached −166 μA, a 6.1% increase over the amplitude required to evoke an action potential in the neural axon 210 when not coupled with a conditioning pre-pulse. The transmembrane voltage representing the lack of an action potential just prior to the stimulation pulse reaching −166 μA is shown in FIG. 13d. Notably, as shown in FIG. 13f, the application of the conditioning pre-pulse rapidly increases the m-gate openness probability, while slowly decreasing the h-gate openness probability. While increasing the m-gate openness probability initially renders the neural axon 210 more excitable at the beginning of the conditioning pulse, the eventual decrease in the h-gate openness probability renders the neural axon 210 less excitable to the subsequently applied stimulation pulse. Thus, as previously described in the background, the use of a long duration, depolarizing, conditioning pulse predominantly operates on the h-gates to render the neural axon 210 less excitable to subsequent stimulation.

Figure 14A:
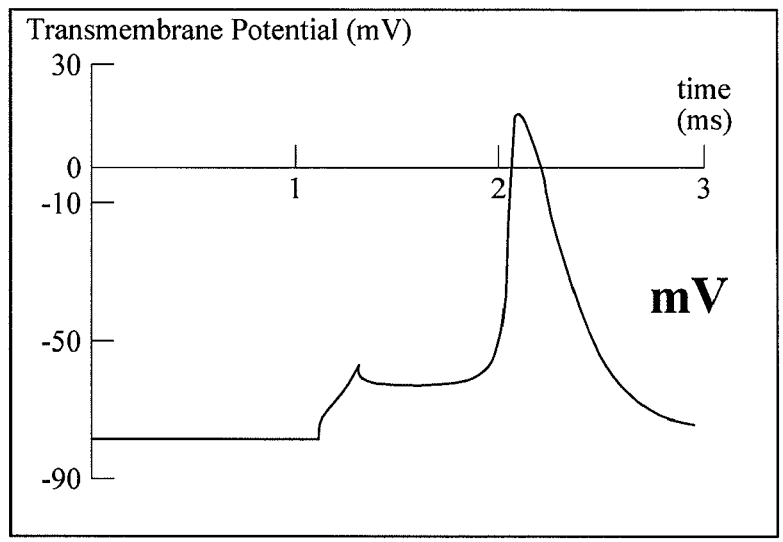
FIGS. 14a-14f are various diagrams illustrating a second case study performed by stimulating the nerve axon of FIG. 12 with a short duration stimulation pulse, alone, and coupled with a long duration, sub-threshold, depolarizing, conditioning pre-pulse.
Figure 14B:
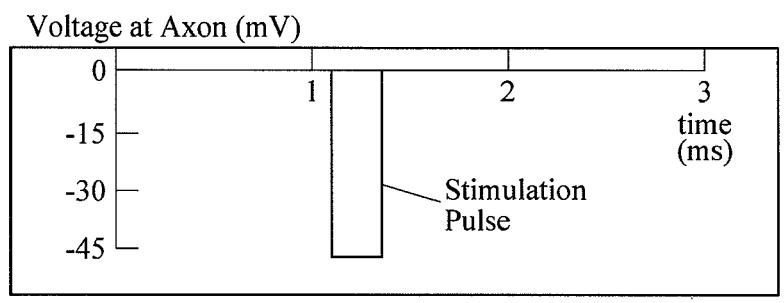
Figure 14C:
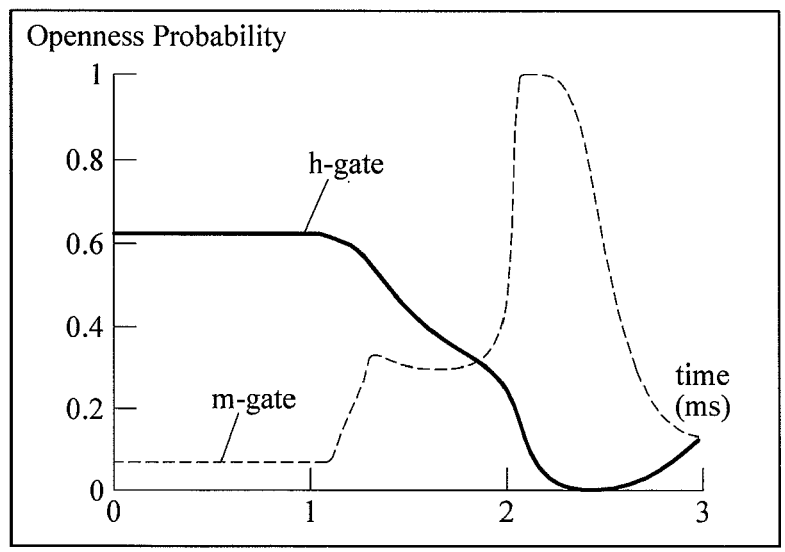

Referring to FIGS. 14a-14f, a second case study was conducted in the same manner as the first case study, with the exception that the stimulation pulse was decreased to a 200 μs duration, and the amplitude of the conditioning pulse was selected to be −2 μA. When applied alone, as shown in FIG. 14b, the amplitude of the stimulation pulse was increased from an initial level until an action potential, as represented by the transmembrane voltage in FIG. 14a, was evoked in the neural axon 210. An action potential was found to occur when the amplitude of the stimulation pulse reached −243 μA. In a manner similar to the first case study, up until the stimulation pulse is applied (when the neural axon 210 is at rest), the m-gate openness probability is maintained at a very low level, and the h-gate openness probability is maintained at a very high level, as illustrated in FIG. 14c, so that the neural axon 210 is nominally excitable to the subsequent stimulation pulse.

Figure 14D:
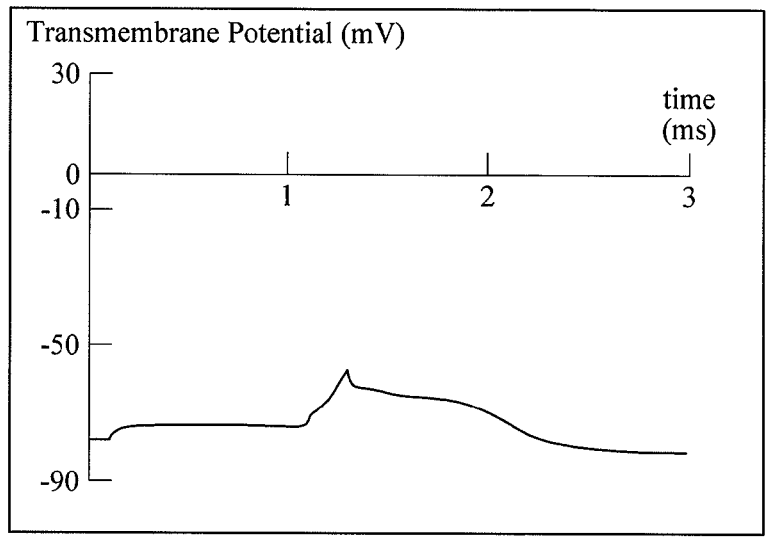
Figure 14E:
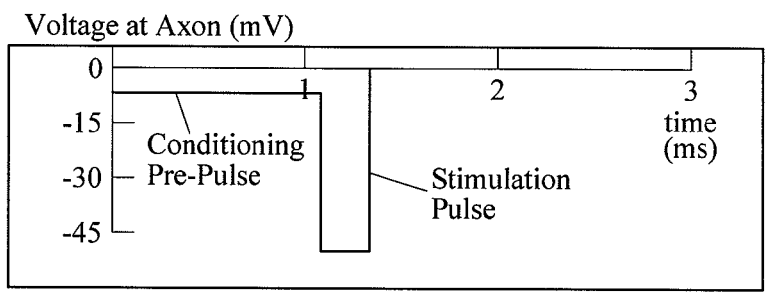
Figure 14F:
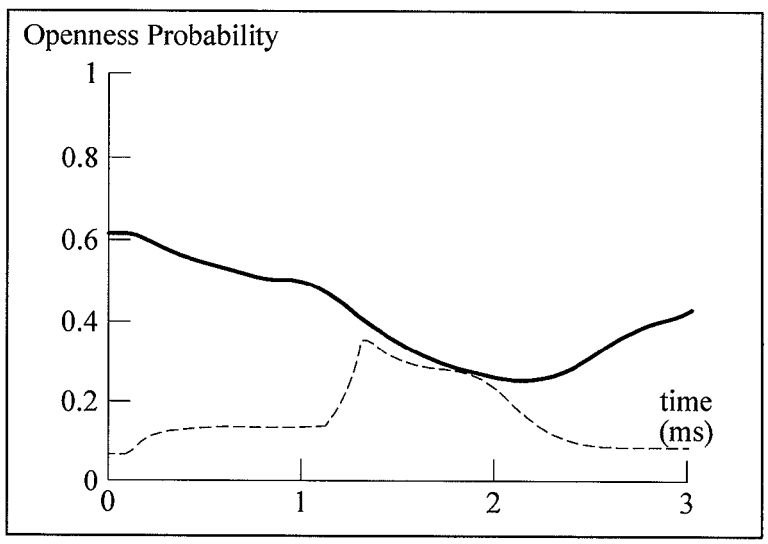

In contrast, when coupled with the depolarizing conditioning pre-pulse, as shown in FIG. 14e, the amplitude of the stimulation pulse was increased from an initial level until an action potential was evoked in the neural axon 210. An action potential was found to occur when the amplitude of the stimulation pulse reached −245 µA, only a 0.8% increase over the amplitude required to evoke an action potential in the neural axon 210 when not coupled with a conditioning pre-pulse. The transmembrane voltage representing the lack of an action potential just prior to the stimulation pulse reaching −245 µA is shown in FIG. 14d. Notably, as shown in FIG. 14f, the use of a long duration, depolarizing, conditioning pulse predominantly operates on the h-gates to render the neural axon 210 less excitable to the subsequently applied stimulation pulse. However, due to the shortening of the stimulation pulse duration, the effect of the conditioning pre-pulse illustrated in FIG. 14e is minimal. Significantly, the effectiveness of this conditioning pre-pulse would be even more diminished at much lower stimulation pulse durations (e.g., 50 µs).

Referring to FIGS. 15a-15f, a third case study was conducted in the same manner as the first case study, with the exception that a sub-threshold, hyperpolarizing, conditioning pre-pulse, instead of a sub-threshold, depolarizing, conditioning pre-pulse, was used. In this case study, the conditioning pre-pulse is anodic, and the stimulation pulse is cathodic, the stimulation pulse was selected to have a duration of 50 µs, the conditioning pre-pulse was selected to have a duration of 50 µs and an amplitude level of 30 µA, and the delay between the conditioning pre-pulse and the stimulation pulse was selected to be zero.

Figure 15A:
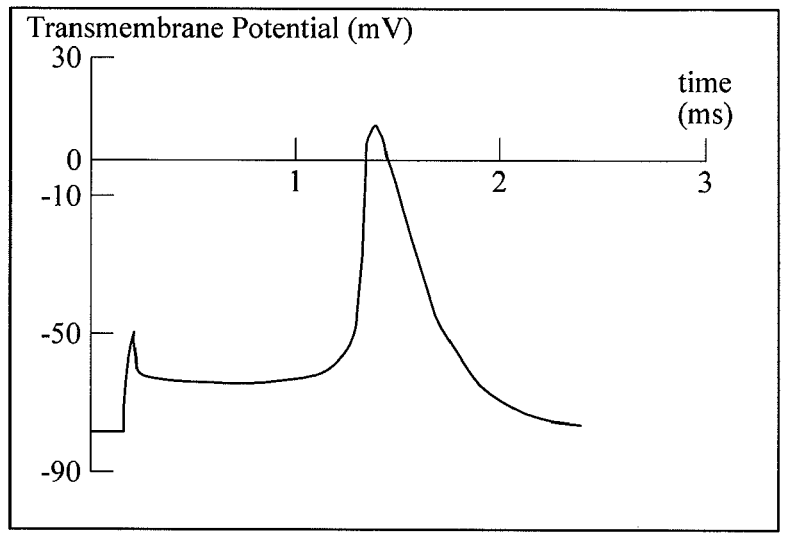
FIGS. 15a-15f are various diagrams illustrating a third case study performed by stimulating the nerve axon of FIG. 12 with a short duration stimulation pulse, alone, and coupled with a short duration, sub-threshold, hyperpolarizing, conditioning pre-pulse.
Figure 15B:
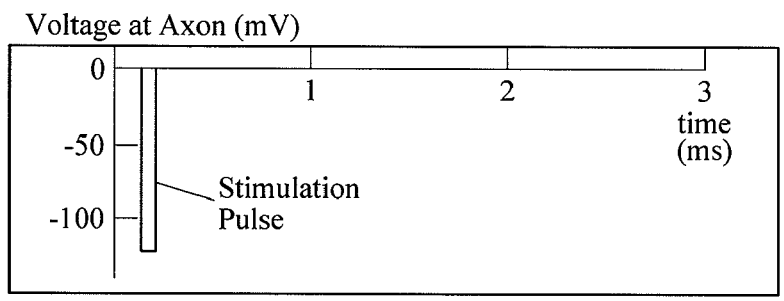
Figure 15C:
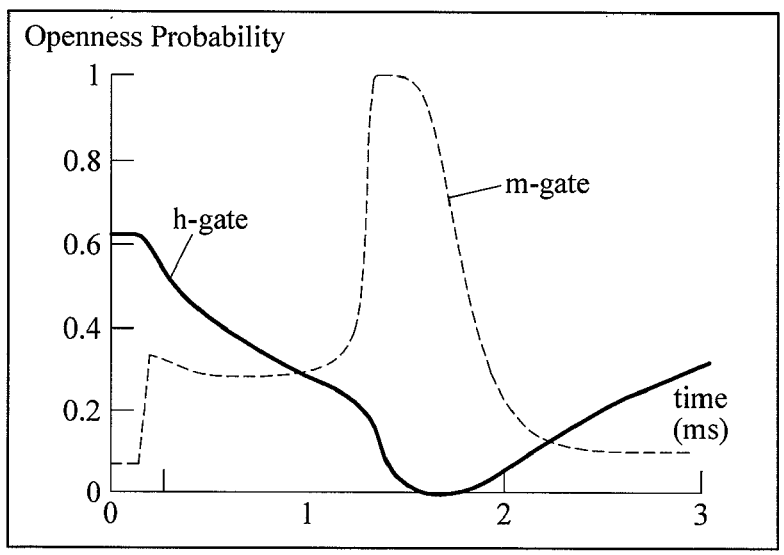

When applied alone, as shown in FIG. 15b, the amplitude of the stimulation pulse was increased from an initial level until an action potential, as represented by the transmembrane voltage in FIG. 15a, was evoked in the neural axon 210. An action potential was found to occur when the amplitude of the stimulation pulse reached −628 µA. In a manner similar to the first case study, up until the stimulation pulse is applied (when the neural axon 210 is at rest), the m-gate openness probability is maintained at a very low level, and the h-gate openness probability is maintained at a very high level, as illustrated in FIG. 15c, so that the neural axon 210 is nominally excitable to the subsequent stimulation pulse.

Figure 15D:
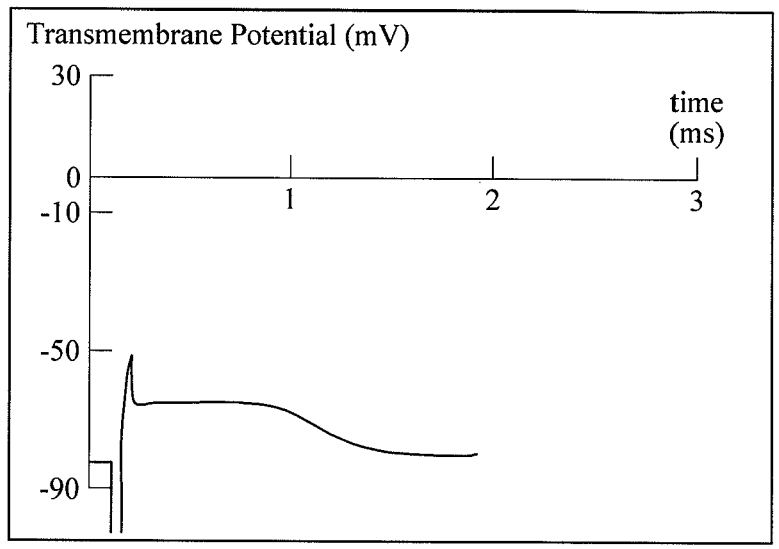
Figure 15E:
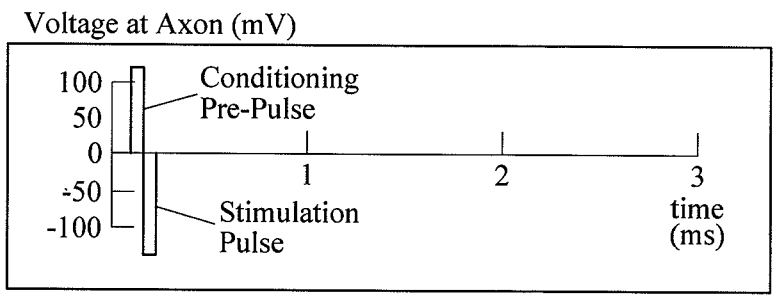
Figure 15F:
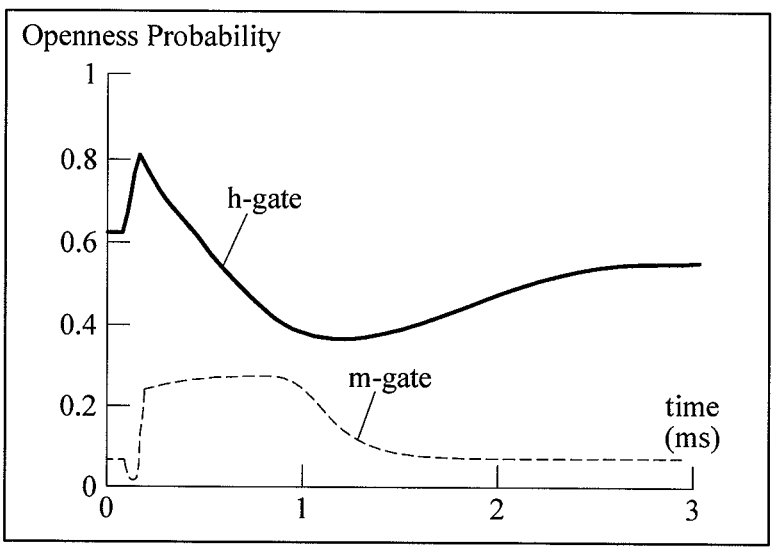

In contrast, when coupled with a hyperpolarizing conditioning pre-pulse, as shown in FIG. 15e, the amplitude of the stimulation pulse was increased from an initial level until an action potential was evoked in the neural axon 210. An action potential was found to occur when the amplitude of the stimulation pulse reached −702 µA, an 11.7% increase over the amplitude required to evoke an action potential in the neural axon 210 when not coupled with a conditioning pre-pulse. Notably, the use of this hyperpolarizing, conditioning, pre-pulse increased the threshold of the neural axon 210 twice as much as the long duration, depolarizing condition pre-pulse did in the first case study. The transmembrane voltage representing the lack of an action potential just prior to the stimulation pulse reaching −702 µA is shown in FIG. 15d. Notably, as shown in FIG. 15f, the application of the conditioning pre-pulse decreases the m-gate openness probability. Significantly, due to the relatively short duration of the conditioning pre-pulse, the h-gate openness probability is not drastically affected. That is, because the h-gates have a higher time constant than do the m-gates, the use of a short duration, hyperpolarizing, conditioning pulse predominantly operates on the m-gates to render the neural axon 210 less excitable to the subsequently applied stimulation pulse. Notably, although the time constant differences between the h-gates and m-gates are difficult to see in FIG. 15f due to scaling, a close-up of FIG. 15f would reveal that the h-gate openness probability increases well after the m-gate openness probability increases.

Figure 16A:
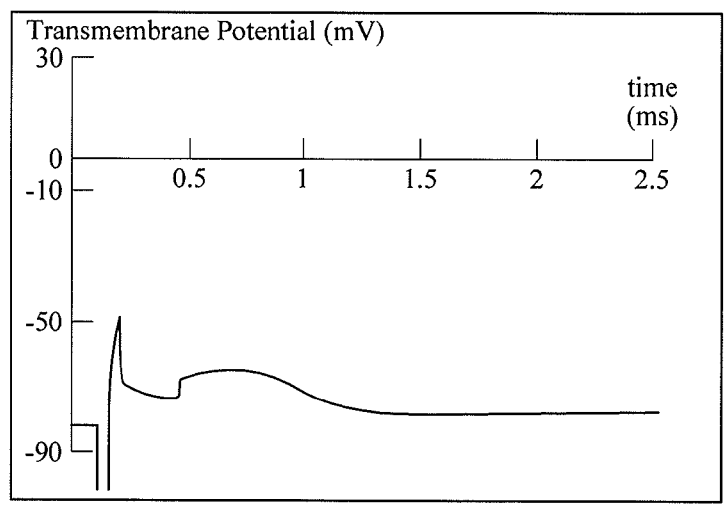
FIGS. 16a-16c are various diagrams illustrating a fourth case study performed by stimulating the nerve axon of FIG. 12 with a short duration stimulation pulse coupled with a short duration, sub-threshold, hyperpolarizing, conditioning pre-pulse, and a sub-threshold, hyperpolarizing, conditioning post-pulse.
Figure 16B:
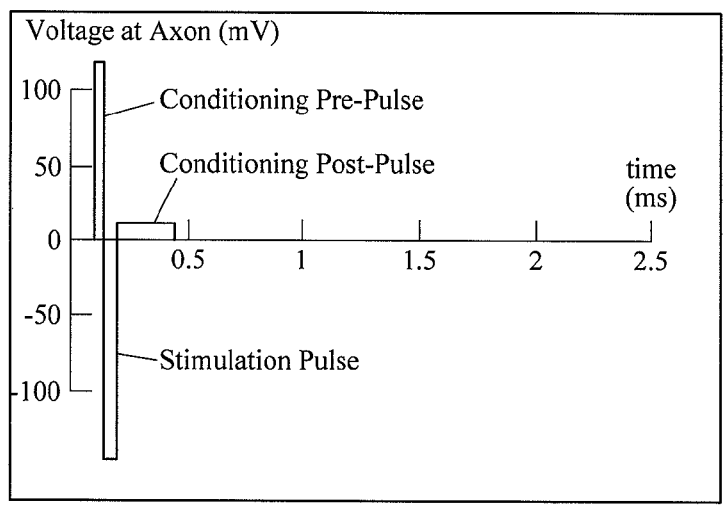
Figure 16C:
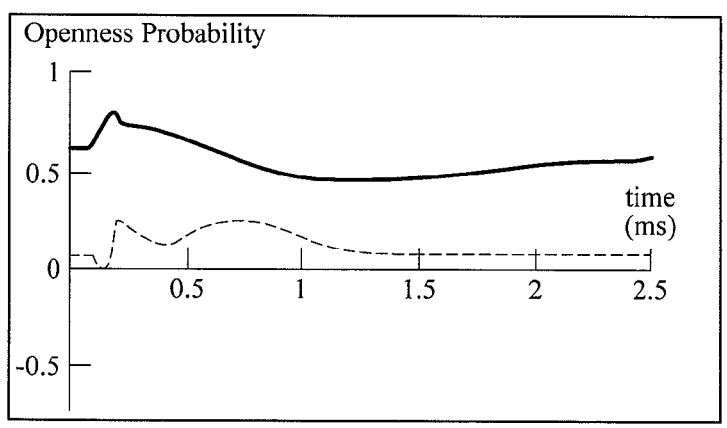

Referring to FIGS. 16a-16c, a fourth case study was conducted in the same manner as the third case study, with the exception that a sub-threshold, hyperpolarizing, conditioning post-pulse was used in addition to the hyperpolarizing, conditioning pre-pulse. In this case study, the conditioning post-pulse is anodic, the conditioning post-pulse was selected to have a duration of 250 µs and an amplitude level of 2.5 µA, and the delay between the stimulation pulse and the conditioning post-pulse was selected to be zero.

When coupled with a hyperpolarizing conditioning pre-pulse and a hyperpolarizing conditioning post-pulse, as shown in FIG. 16b, the amplitude of the stimulation pulse was increased from an initial level until an action potential was evoked in the neural axon 210. An action potential was found to occur when the amplitude of the stimulation pulse reached −743 µA, an 18.3% increase over the amplitude required to evoke an action potential in the neural axon 210 when not coupled with a conditioning pre-pulse and conditioning post-pulse. The transmembrane voltage representing the lack of an action potential just prior to the stimulation pulse reaching −743 µA is shown in FIG. 16a. Notably, as shown in FIG. 16c, the application of the conditioning post-pulse decreases the m-gate openness probability after the stimulation pulse is applied to render the neural axon 210 even less excitable to the previously applied stimulation pulse. Notably, as shown in FIG. 16c, the m-gates have a rebound-opening effect at the end of the conditioning post-pulse, suggesting that a post-pulse that tapers in time may be more effective than a post-pulse ending in a strong discontinuity.

Figure 17A:
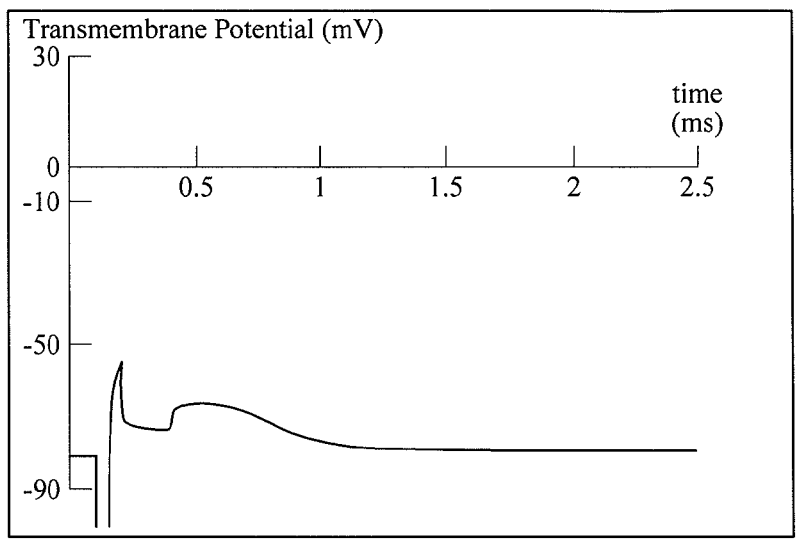
FIGS. 17a-17c are various diagrams illustrating a fifth case study performed by stimulating the nerve axon of FIG. 12 with a short duration stimulation pulse coupled with a short duration, sub-threshold, hyperpolarizing, conditioning pre-pulse, a sub-threshold, hyperpolarizing, conditioning concurrent pulse, and a sub-threshold, hyperpolarizing, conditioning post-pulse.
Figure 17B:
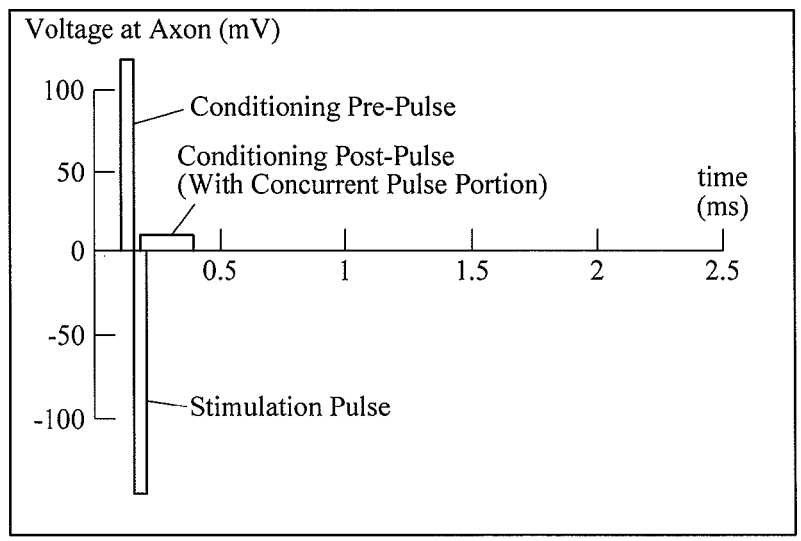
Figure 17C:
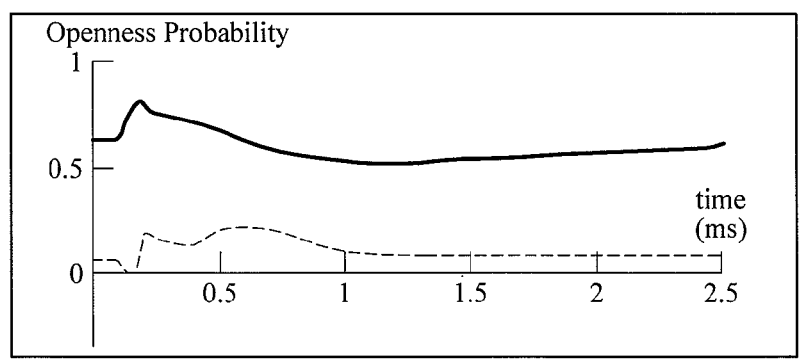

Referring to FIGS. 17a-17c, a fifth case study was conducted in the same manner as the fourth case study, with the exception that the conditioning post-pulse overlaps the stimulation pulse by 100 µs. That is, the initial portion of the post-pulse is actually a concurrent conditioning pulse. As shown in FIG. 17b, the amplitude of the stimulation pulse was increased from an initial level until an action potential was evoked in the neural axon 210. An action potential was found to occur when the amplitude of the stimulation pulse reached −782 µA, a 24.5% increase over the amplitude required to evoke an action potential in the neural axon 210 when not coupled with a conditioning pre-pulse and conditioning post-pulse. The transmembrane voltage representing the lack of an action potential just prior to the stimulation pulse reaching −782 µA is shown in FIG. 17a. Notably, as shown in FIG. 17c, the application of the conditioning concurrent pulse decreases the m-gate openness probability during application of the stimulation pulse (i.e., during the last 100 µs of the stimulation pulse), and the application of the conditioning concurrent-pulse and post-pulse decreases the m-gate openness probability after the stimulation pulse is applied, to render the neural axon 210 even less excitable to the stimulation pulse.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient, comprising placing at least one electrode in contact with tissue of a patient;
conveying a sub-threshold, hyperpolarizing, conditioning pre-pulse from the at least one electrode that renders a first region of the tissue less excitable to stimulation; and
conveying a depolarizing stimulation pulse from the at least one electrode to stimulate a second different region of the tissue, wherein the duration of the conditioning pre-pulse is equal to or shorter than the stimulation pulse.

2. The method of claim 1, wherein the at least one electrode comprises a first electrode and a second electrode, the conditioning pre-pulse is conveyed from the first electrode, and the stimulation pulse is conveyed from the second electrode.

3. The method of claim 1, wherein the conditioning pre-pulse is anodic, and the stimulation pulse is cathodic.

4. The method of claim 1, wherein the first tissue region comprises dorsal root nerve fibers, and the second tissue region comprises dorsal column nerve fibers.

5. The method of claim 1, wherein the conditioning pre-pulse has a duration less than 200 µs.

6. The method of claim 1, wherein the conditioning pre-pulse has a duration equal to or less than 150 µs.

7. The method of claim 1, wherein the conditioning pre-pulse has a duration equal to or less than 75 µs.

8. The method of claim 1, further comprising conveying a sub-threshold, hyperpolarizing conditioning post-pulse from the at least one electrode to further render the first tissue region less excitable to the stimulation pulse.

9. The method of claim 8, wherein the conditioning post-pulse overlaps the at least one stimulation pulse in time.

10. The method of claim 8, wherein the first tissue region has at least one neural axon having a plurality of m-gates located in the membrane of the at least one neural axon, and wherein the conditioning post-pulse further renders the first tissue region less excitable to the previously applied stimulation pulse by decreasing the openness probability of the plurality of m-gates.

11. The method of claim 1, wherein the first tissue region has at least one neural axon having a plurality of m-gates and a plurality of h-gates located in the membrane of the at least one neural axon, and wherein the conditioning pre-pulse renders the first tissue region less excitable to stimulation by predominantly acting on the plurality of m-gates relative to the plurality of h-gates.

12. The method of claim 11, wherein the conditioning pre-pulse predominantly acts on the plurality of m-gates by decreasing the openness probability of the plurality of m-gates while not substantially affecting the openness probability of the plurality of h-gates.

13. The method of claim 1, wherein the first tissue region comprises one of dorsal column nerve fibers and dorsal root nerve fibers, and the second tissue region comprises the other of the dorsal column nerve fibers and the dorsal root nerve fibers.

14. The method of claim 1, wherein the first tissue region and the second tissue region comprises spinal nerve tissue.

15. A method of providing therapy to a patient, comprising:
placing at least one electrode in contact with spinal nerve tissue of a patient;
conveying a sub-threshold, hyperpolarizing, conditioning pre-pulse from the at least one electrode to the tissue, wherein the conditioning pre-pulse has a duration less than 200 µs; and
conveying a depolarizing stimulation pulse from the at least one electrode to the tissue, wherein the duration of the conditioning pre-pulse is equal to or shorter than the stimulation pulse.

16. The method of claim 15, wherein the at least one electrode comprises a first electrode and a second electrode, the conditioning pre-pulse is conveyed from the first electrode to the tissue, and the stimulation pulse is conveyed from the second electrode to the tissue.

17. The method of claim 15, wherein the conditioning pre-pulse is anodic, and the stimulation pulse is cathodic.

18. The method of claim 15, wherein the conditioning pre-pulse has a duration equal to or less than 150 µs.

19. The method of claim 15, wherein the conditioning pre-pulse has a duration equal to or less than 75 µs.

20. The method of claim 15, wherein the stimulation pulse has a duration less than 200 µs.

21. The method of claim 15, further comprising conveying a sub-threshold, hyperpolarizing conditioning post-pulse from the at least one electrode to the tissue, thereby modifying the effect that the stimulation pulse has on the tissue.

22. The method of claim 21, wherein the conditioning post-pulse overlaps the at least one stimulation pulse in time.

23. The method of claim 21, wherein the tissue has at least one neural axon having a plurality of m-gates located in the membrane of the at least one neural axon, and wherein the conditioning post-pulse decreases the openness probability of the plurality of m-gates.

24. The method of claim 15, wherein the tissue has at least one neural axon having a plurality of m-gates and a plurality of h-gates located in the membrane of the at least one neural axon, and wherein the conditioning pre-pulse predominantly acts on the plurality of m-gates relative to the plurality of h-gates.

25. The method of claim 24, wherein the conditioning pre-pulse predominantly acts on the plurality of m-gates by decreasing the openness probability of the plurality of m-gates while not substantially affecting the openness probability of the plurality of h-gates.

* * * * *